United States Patent
Gradon et al.

(10) Patent No.: US 8,636,005 B2
(45) Date of Patent: Jan. 28, 2014

(54) BREATHING ASSISTANCE APPARATUS

(75) Inventors: Lewis George Gradon, Auckland (NZ); Alastair Edwin McAuley, Auckland (NZ); Teresa Anne Joe, Bristol (GB); Neil Glen Davies, Auckland (NZ); Tracey Carolyn Winstone, Auckland (NZ); Ivan Milivojevic, London (GB)

(73) Assignee: Fisher & Paykel Healthcare Limited, Auckland (NZ)

( * ) Notice: Subject to any disclaimer, the term of this patent is extended or adjusted under 35 U.S.C. 154(b) by 951 days.

(21) Appl. No.: 10/575,324

(22) PCT Filed: Oct. 8, 2004

(86) PCT No.: PCT/NZ2004/000246
§ 371 (c)(1),
(2), (4) Date: Apr. 4, 2007

(87) PCT Pub. No.: WO2005/032634
PCT Pub. Date: Apr. 14, 2005

(65) Prior Publication Data
US 2007/0175480 A1    Aug. 2, 2007

(30) Foreign Application Priority Data
Oct. 8, 2003 (NZ) ..................... 528800

(51) Int. Cl.
*A62B 18/08* (2006.01)
*A62B 18/02* (2006.01)

(52) U.S. Cl.
USPC ............ 128/207.11; 128/206.21; 128/207.13

(58) Field of Classification Search
USPC ............ 128/201.24, 203.29, 205.25, 206.21, 128/206.24, 206.28, 207.11
See application file for complete search history.

(56) References Cited

U.S. PATENT DOCUMENTS

| 4,934,361 | A | * | 6/1990 | Michel et al. ............ 128/206.17 |
| 4,938,209 | A | | 7/1990 | Fry |
| 5,087,118 | A | * | 2/1992 | Gill ............................. 351/156 |
| 5,449,206 | A | | 9/1995 | Lockwood |
| 5,586,969 | A | * | 12/1996 | Yewer, Jr. ....................... 602/19 |
| 5,687,715 | A | * | 11/1997 | Landis et al. ............ 128/207.18 |
| 6,044,844 | A | * | 4/2000 | Kwok et al. .............. 128/207.11 |
| 6,347,631 | B1 | | 2/2002 | Hansen et al. |
| 6,470,886 | B1 | * | 10/2002 | Jestrabek-Hart ......... 128/207.11 |
| 6,595,214 | B1 | * | 7/2003 | Hecker et al. ............ 128/207.13 |
| 7,290,546 | B2 | * | 11/2007 | Sprinkle et al. .......... 128/206.24 |
| 7,527,057 | B2 | * | 5/2009 | Fecteau et al. ........... 128/206.27 |

(Continued)

FOREIGN PATENT DOCUMENTS

| AU | 200071882 A1 * | 6/2001 |
| AU | 783657 | 11/2005 |

(Continued)

*Primary Examiner* — Patricia Bianco
*Assistant Examiner* — Rachel Young
(74) *Attorney, Agent, or Firm* — Knobbe, Martens, Olson & Bear LLP

(57) ABSTRACT

A user interface (22) with headgear (29) is disclosed where a flexible conduit (24) supplies gases to the patient interface and the conduit is connected to the headgear by a sliding connection or support portion (26). In one form headgear may include a transverse strap which the conduit is attached to. In other forms various sliding straps constrain the conduit such that forces on the conduit are transferred to the headgear not the interface. Interface vertical height and angular adjustment mechanisms are also disclosed.

15 Claims, 20 Drawing Sheets

(56) References Cited

U.S. PATENT DOCUMENTS

| | | | |
|---|---|---|---|
| 2001/0042547 A1* | 11/2001 | McDonald et al. | 128/207.11 |
| 2002/0014241 A1* | 2/2002 | Gradon et al. | 128/205.25 |
| 2002/0026934 A1 | 3/2002 | Lithgow et al. | |
| 2002/0056457 A1* | 5/2002 | Demers et al. | 128/206.27 |
| 2002/0078953 A1* | 6/2002 | Fecteau et al. | 128/202.27 |
| 2003/0196662 A1* | 10/2003 | Ging et al. | 128/204.15 |
| 2004/0035427 A1 | 2/2004 | Bordewick et al. | |
| 2006/0118119 A1* | 6/2006 | Berthon-Jones et al. | 128/207.11 |

FOREIGN PATENT DOCUMENTS

| | | |
|---|---|---|
| WO | WO 82/03548 | 10/1982 |
| WO | WO 98/24499 | 6/1998 |
| WO | WO 98/48878 | 11/1998 |
| WO | WO 03/092755 | 11/2003 |
| WO | WO 2004/030736 | 4/2004 |
| WO | WO 2005/018523 | 3/2005 |

* cited by examiner

BREATHING ASSISTANCE APPARATUS

FIELD OF INVENTION

This invention relates to patient or user interfaces particularly though not solely for use in delivering artificial respiration therapy to patients requiring respiratory humidification treatment. In particular the present invention relates to a mask with improved headgear.

BACKGROUND OF THE INVENTION

In the art of respiration devices, there are a well known variety of respiratory masks which cover the nose and/or mouth of a human user in order to provide a continuous seal around the nasal and/or oral areas of the user's face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

In common with prior art designs, is an inability to attach the plenum, supplying gases to the user, to the head strap such that the position of the plenum may be altered without distorting the position of the mask on the user's face.

U.S. Pat. No. 6,347,631 and U.S. Pat. No. 6,516,802 are examples of prior art that provide a means of rigidly attaching a gas plenum to the hear gear which utilises a cantilever adjustment mechanism. The cantilever adjustment mechanism provides a means of adjusting the headgear and any movement of the gas plenum is achieved by sliding the plenum through a plurality of rings on the cantilever arrangement.

SUMMARY OF THE INVENTION

It is an object of the present invention to attempt to provide an interface and headgear which goes some way to overcoming the abovementioned disadvantages in the prior art or which will at least provide the industry with a useful choice. Accordingly in a first aspect the present invention consists in a device for delivering a supply of gases to a user comprising or including:

an interface including a hollow body, a gases inlet and a sealing member configured to in use rest against the face of a user, adapted in use to supply gases to said user, a conduit supplying said gases to said interface, said conduit attached to an inlet to said hollow body, and headgear adapted to attach to said interface and around the head of said user, where said conduit is supported in relation to said headgear such that any load on said conduit is taken by said headgear and not said interface.

In another aspect the invention can be said to broadly consist of a device for delivering a supply of gases to a user comprising or including:

an interface including a hollow body, a gases inlet and a sealing member configured to in use rest against the face of a user, adapted in use to supply gases to said user, a conduit supplying said gases to said interface, said conduit attached to an inlet to said hollow body, and headgear adapted to attach to said interface and around the head of said user, where said conduit includes at least one angular adjustment mechanism to allow for angular adjustment of said interface, and a sling connected to said headgear, said sling to connect to and support said conduit.

In a further aspect the invention can be said to broadly consist of a device for delivering a supply of gases to a user comprising or including:

an interface including a hollow body, a gases inlet and a sealing member configured to in use rest against the face of a user, adapted in use to supply gases to said user, a conduit supplying said gases to said interface, said conduit attached to an inlet to said hollow body, a headgear adapted to attach to said interface and around the head of said user, and a support strap attached to said headgear, said support strap forming a loop to connect to and support said conduit.

BRIEF DESCRIPTION OF THE DRAWINGS

Preferred forms of the present invention will now be described with reference to the accompanying drawings.

DETAILED DESCRIPTION OF THE PREFERRED EMBODIMENTS

The present invention provides improvements in the delivery of respiratory therapy. In particular an interface is described which is comfortable for the user to wear and significantly reduces the movement of the interface on the user's face as compared with the prior art. It will be appreciated that the interface as described in the preferred embodiment of the present invention can be used in respiratory care generally or with a ventilator but will now be described below with reference to use in a humidified Continuous Positive Airway Pressure (CPAP) system. It will also be appreciated that the present invention can be applied to nasal masks, oral masks, and combination nasal-oral masks.

Figure 1:
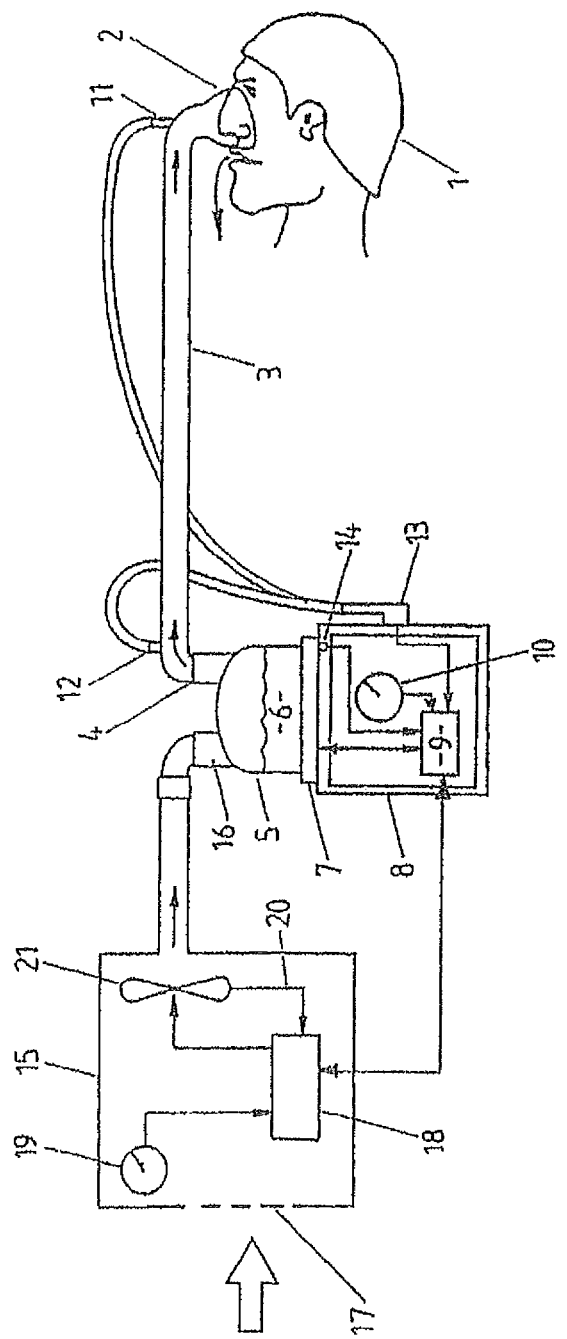
FIG. 1 is a block diagram of a humidified continuous positive airway pressure (CPAP system) as might be used in conjunction with the interface of the present invention.

With reference to FIG. 1 a humidified CPAP system is shown in which a user or patient 1 is receiving humidified and pressurised gases through an interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to user 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within the humidification chamber 5 is heated, water vapour begins to fill the volume of the chamber above the water's surface. The water vapour is then passed out of the humidification chamber 5 outlet 4 with the flow of gases (for example air) provided from a gases supply means or blower 15 which enters the chamber through inlet 16. Exhaled gases from the user's mouth are passed directly to ambient surroundings in FIG. 1.

Blower 15 is provided with variable pressure regulating means or variable speed fan 21 which draws air or other gases through blower inlet 17. The speed of variable speed fan 21 is controlled by an electronic controller 18 (or alternatively the function of controller 18 could be carried out by controller 9) in response to inputs from the controller 9 and a user set predetermined required value (preset value) of pressure or the fan speed via dial 19.

Respiratory Mask

Figure 2:
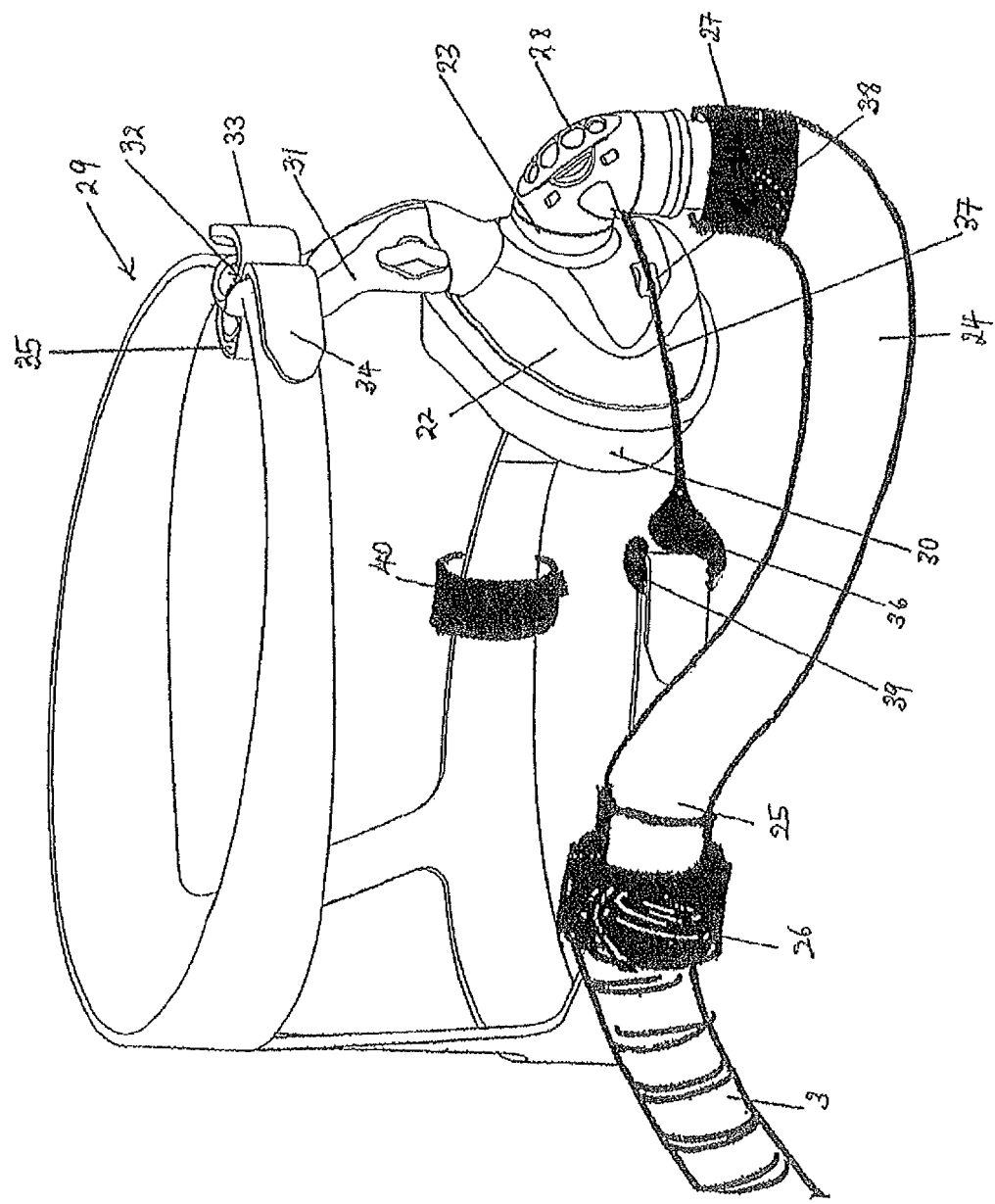
FIG. 2 is an illustration of a first embodiment of the interface of the present invention where slideable hook and loop attachments are provided to attach the gases conduit to the interface headgear.

According to a first embodiment of the present invention the interface is shown in FIG. 2 as a nasal-oral mask. It will be appreciated the interface could equally be a nasal mask, oral mask or nasal-oral mask. The mask 2 includes a hollow body 22, with an inlet 23 connected to a section of flexible tubing 24, and a mask cushion 30. The flexible tubing's free end 25 preferably has a friction fit connector 26 which mates with the inspiratory conduit 3, which supplies gases to the mask inlet 23. The other end of the flexible tubing is connected by known methods to the inlet 23 of the mask 2. As shown in FIG. 2 an outlet bias vent part 28 is disposed between the other end 27 of the flexible tubing 24. The outlet vent part 28 allows gases expired by the user to be vented. The mask 2 is positioned on the face of the user 1 with headgear 29, including at least one strap secured around the back of the head of the user 1. The restraining force from the headgear 29 on the hollow body 22 ensures enough compressive force on the mask cushion 30 to provide an effective seal against the user's face.

The hollow body 22 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Forehead Rest

Referring to FIG. 2, the mask 2 includes a bridge member 31 that is substantially I shaped and has the purpose of providing a forehead rest for the user. Harnessing slots 32 are provided at the top end of the bridge member 31 which receive and enable the securement of straps 33, 34 from the headgear 29 to secure the mask 2 to the headgear 29 and user's face. For the users comfort one or more resilient cushions 35 are provided on bridge member 31 to rest on the forehead of the user. The cushions 35 are constructed by injection moulding or extruding, from silicon or any other foam materials as is known in the art for providing cushioning. In other forms of the interface, such as that interface shown in FIGS. 5 and 6, the bridge member 56 may be a T-shaped forehead rest having cushions similar to that described above.

Mask Headgear

Figure 7:
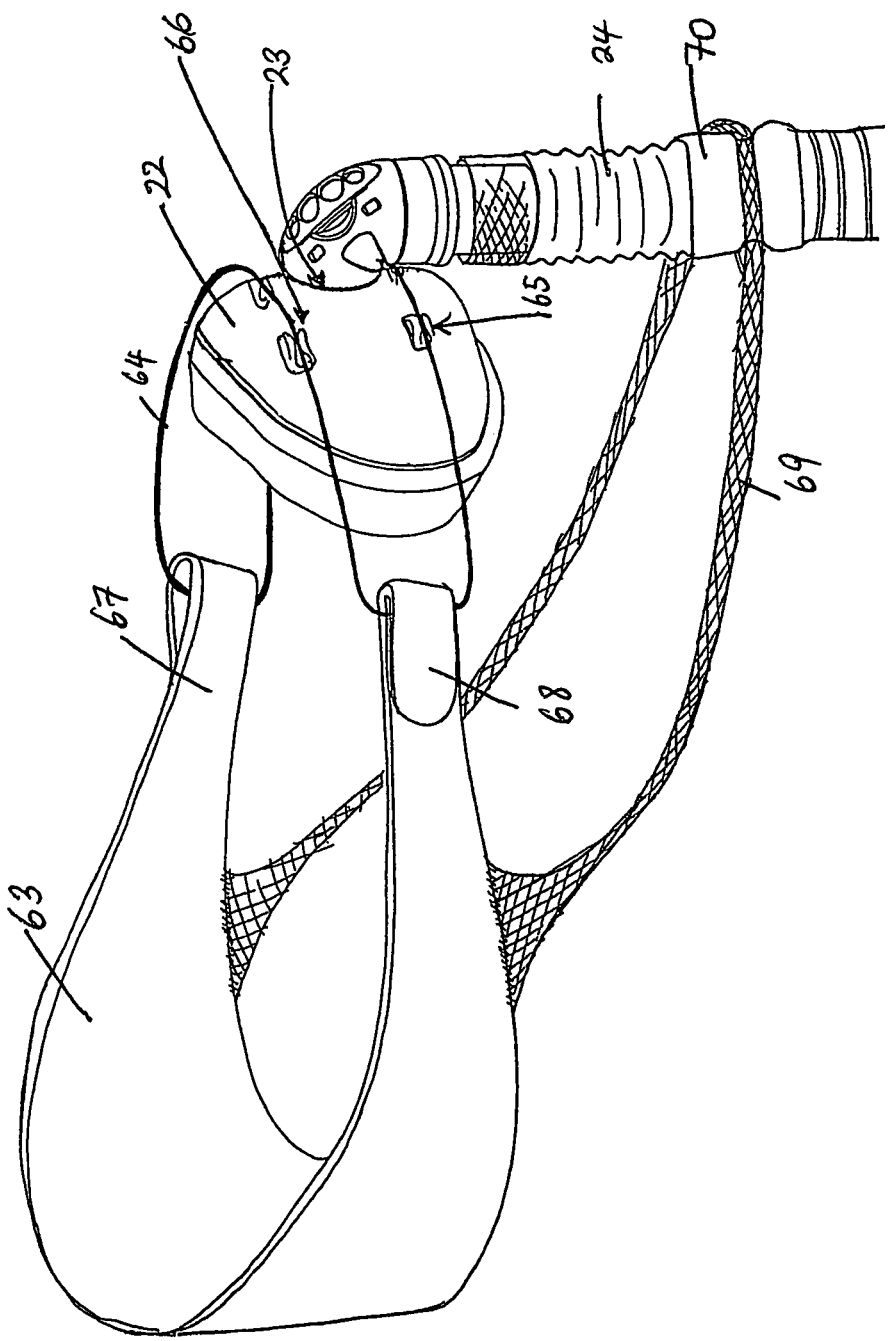
FIG. 7 is an illustration of a fifth embodiment of the interface of the present invention, where an additional support strap is provided between the headgear and gases conduit.
Figure 8:
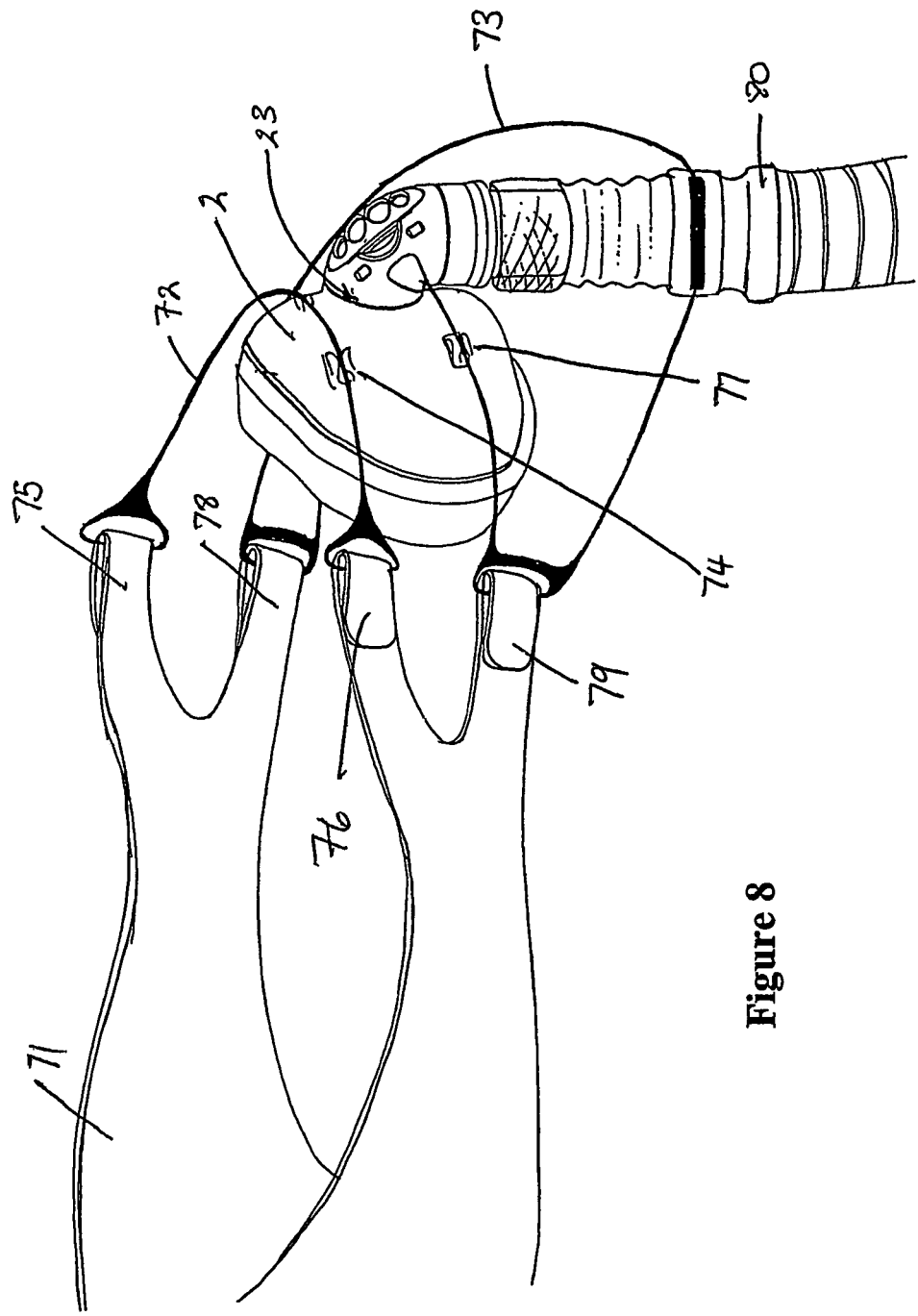
FIG. 8 an illustration of a sixth embodiment of the interface of the present invention, where an additional, but alternative, support strap is provided between the headgear and gases conduit.

To ensure user comfort and effective pressure on the mask cushion, the headgear 29 may be constructed either using two straps running around the back of the user's head as shown in FIG. 2 or with a wider single strap or any other configurations as are known in the art. For example, the headgear as shown in FIGS. 7 and 8 have headgear that comprises one strap that fits about the back of the user's head. In this case the single or double strap configurations would be constructed using neoprene but may also be constructed using any material as is known in the art that will be comfortable for the user.

Referring back to FIG. 2, the headgear 29 is shown connected to the hollow body 22. Rather than the traditional fixed or adjustable attachments the present invention utilises a sliding strap 36 to attach the headgear to the hollow body 22. The strap 36 is preferably constructed of polyacetyl (Delrin 500P NC010) using injection moulding techniques to give a polished finish. This material, similar to other nylon based derivatives, with its polished finish has a particularly low friction co-efficient, and therefore slides with respect to the hollow body 22 with very little resistance. Such a sliding strap is described in our co-pending New Zealand application number 514184 and is herein included by way of reference.

The sliding strap 36 includes a mid-section 37 intended to reciprocate with the engaging clips 38, terminated at each end by loops 39 (of which only one of the two is shown in FIG. 2) that attach to the headgear 29, for example by hook and loop material, such as VELCRO™, straps.

The hollow body 22 includes at least two engaging clips 38 (of which only one is shown in FIG. 2), where in use the sliding strap 36 snaps into the engaging clips 38 and can only be removed there from using substantial force. This means that with any normal use the sliding strap 36 will stay retained within the engaging clips 38. In other embodiments of the interface and headgear different numbers of clips may be provided in order to allow different headgear and sliding strap configurations, for example, see FIGS. 7 and 8 for alternative clip configurations.

Figure 9:
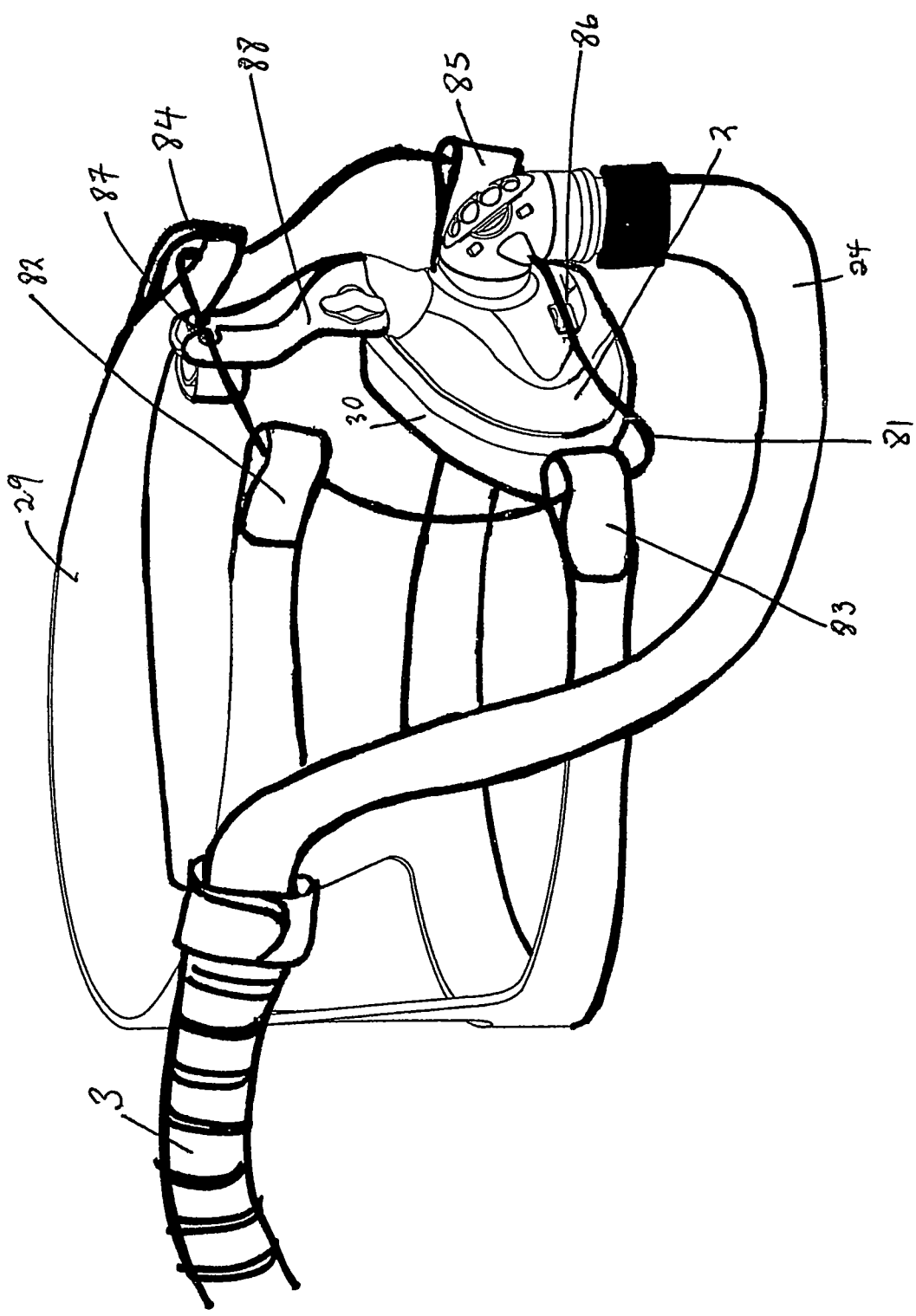
FIG. 9 is an illustration of a seventh embodiment of the interface of the present invention, where a looped gliding strap is provided between the headgear and interface and the gases conduit is fixed to a headgear strap by a hook and loop attachment.

In a further embodiment shown in FIG. 9 the present invention is illustrated using a harness system to attach the mask hollow body to the headgear 29. This harness system comprises a loop 81 of low friction, tough, fatigue resistant cord (or extruded plastic) which engages the headgear 29 through hook and loop attachments 82, 83, 84, 85 to the mask 2 through the engaging clips 26 and slot 87 formed in the bridging member 88 of the mask forehead rest. This system provides for freedom of movement about three mutually perpendicular axes without breaking the seal between the mask cushion 30 and the user's face, and accommodates movement of the flexible tubing 24 and inspiratory conduit 3.

Flexible Tubing Extension Piece

In the preferred embodiment of the present invention a section of highly flexible tubing 24 is provided that attached to the inspiratory conduit 3 and mask inlet 23. In less preferred embodiments of the present invention the inspiratory conduit 3 connects directly to the mask inlet 23.

The flexible tubing 24 is configured to in use connect to the mask inlet 23 while the free end is attached to the inspiratory conduit 3. Therefore, the flexible tubing 24 accommodates movement of the inspiratory conduit 3 (the gases supply line) and movement of the user without affecting the efficiency of the mask seal as any loading on the tubing or conduit is transferred to the headgear. The flexible tubing 24 is preferably a spiral wound tube constructed of a plastics material, for example, polyethylene.

Flexible Tubing Stabilisation

Figure 3:
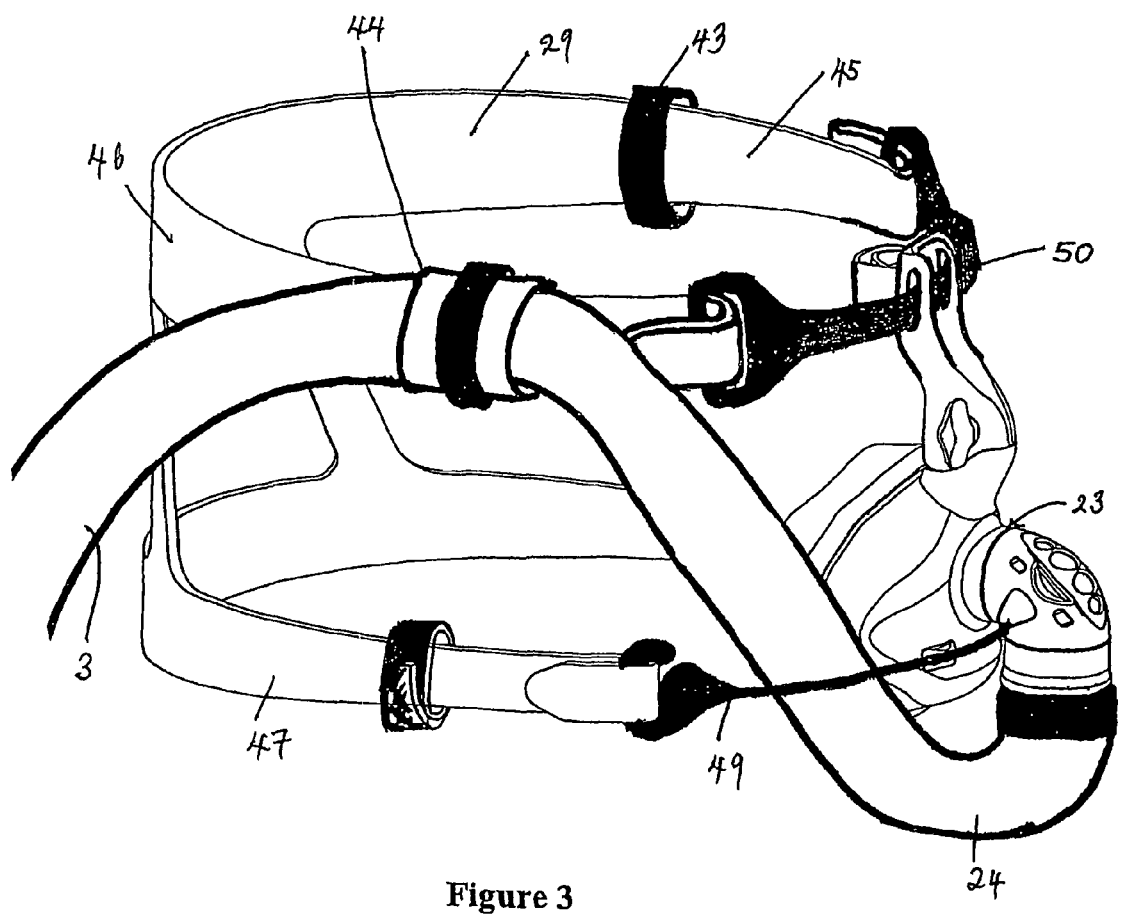
FIG. 3 is a second embodiment of the interface of the present invention.
Figure 5:
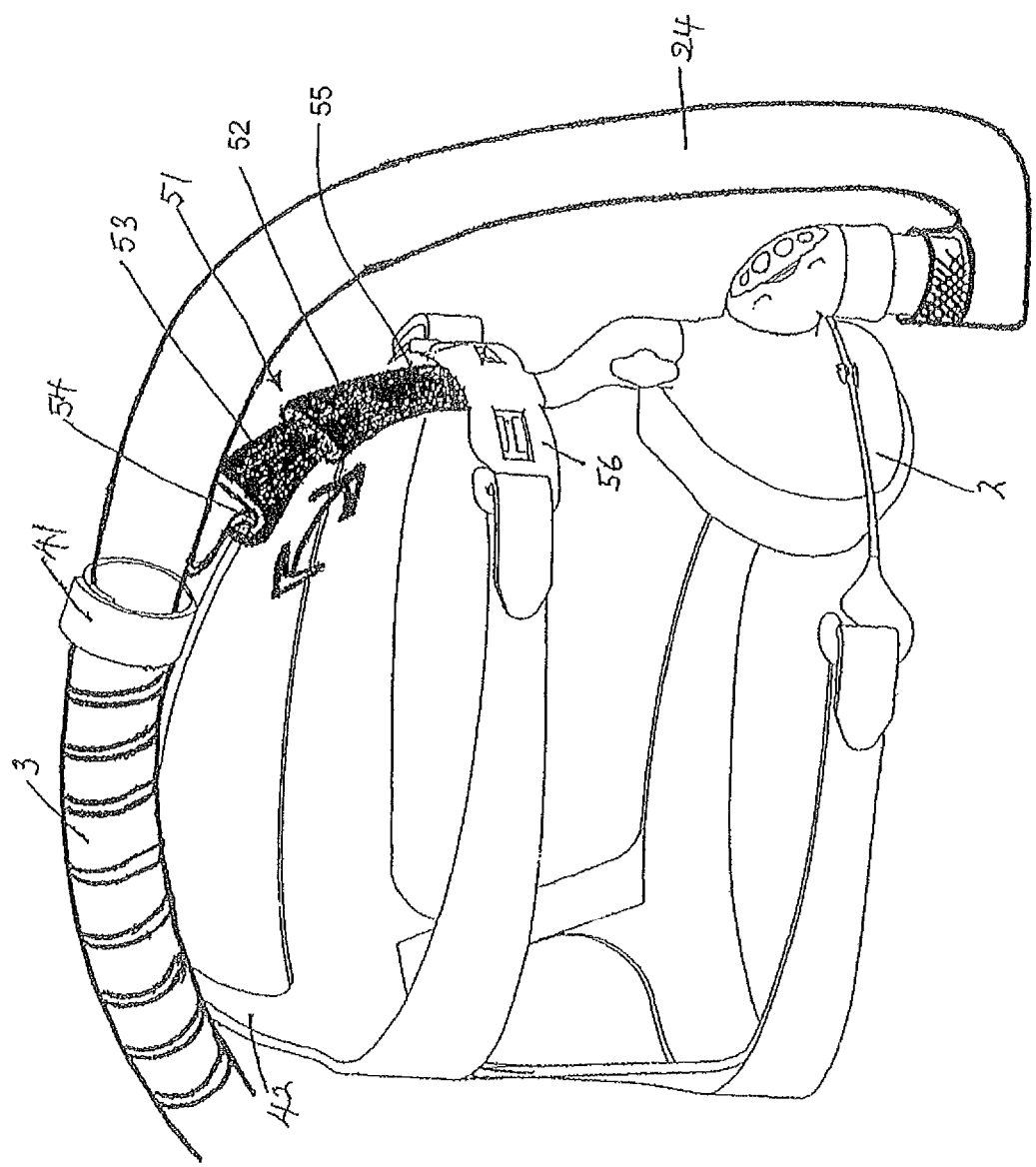
FIG. 5 is an illustration of a third embodiment of the interface of the present invention, where a telescopic extension is provided between the headgear and interface.
Figure 11:
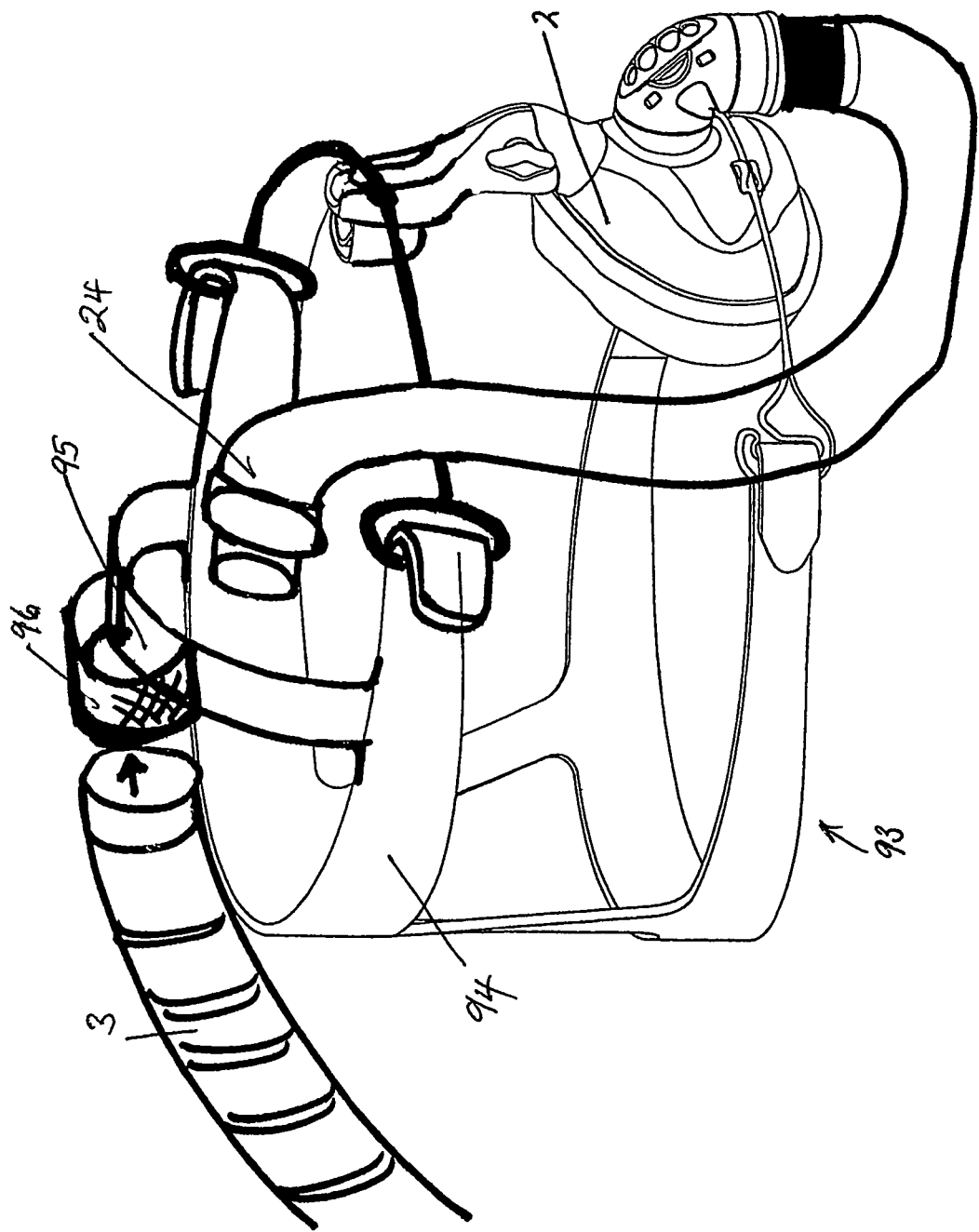
FIG. 11 is an illustration of a ninth embodiment of the interface of the present invention, where the gases conduit is threaded through an alternative loop configuration formed on one of the headgear straps.

A plurality of hook and loop material loops 26, 40, 43, 44 may be slideably attached to the headgear as illustrated in FIG. 2 or 3 to which the connector, the flexible tubing or inspiratory conduit is securely held in position. A similar loop may alternatively be slideably located on headgear that is configured to include a transverse or lateral strap running over the top of the user's head so that the flexible tubing also runs over the top of the user's head. FIG. 5 or 11 show an example of this.

Figure 4:
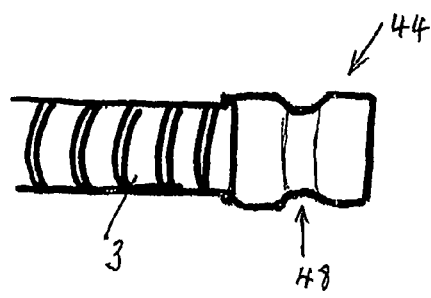
FIG. 4 is an illustration of a contoured connector adapted to connect a first conduit with a second conduit, these conduits supplying gases to the interface.

Alternatively, FIG. 3 shows the flexible tubing 24 connected to the hollow body inlet 23 and an upper headgear strap 46. Here a mechanical attachment, such as a contoured connector 44 as shown in FIG. 4, that is permanently attached, for example, by being moulded about the end of the inspiratory conduit 3. The connector 44 may be attached to any one of the headgear straps 45, 46, 47 in use by fixing a corresponding sliding loop 43, 44, 45 about the recessed part 48 of the connector 44.

In FIG. 3 as well as a lower sliding strap 49 an upper sliding strap 50 is provided to allow the user's more head movement without putting to much load on the mask, preventing the disruption of the seal between the mask and the user's face.

In a further embodiment shown in FIG. 5, the mask and headgear has a telescopic extension mechanism 51 that is constructed in a minimum of two sections. The first section is an outer sheath 52 and the second section is a slideable inner sheath 53, which when not in use resides within the outer sheath 52. The inner sheath's upper end 54 is attached to the transverse headgear strap 41 and the outer sheath bottom end 55 is attached to the rear surface of the mask T-piece forehead rest 56. The transverse strap 42 has a loop 41 (similar to those described previously, but one which is preferably fixed) located on it and functions as a means of securing the connector 44 or merely the flexible tube 24 or inspiratory conduit 3 to the headgear strap 42. The telescopic extension mechanism 51 is constructed from a plastics material, such as acetyl, nylon or polycarbonate, or an elastic type material. The inner sheath 53 has at its upper end a full loop, or other similar fastening mechanism, for connection to the transverse headgear strap 42. Therefore, a degree of movement is allowed such that the position of the inspiratory conduit may be altered without affecting the position of the mask on the user and while maintaining a gas tight seal.

Figure 6:
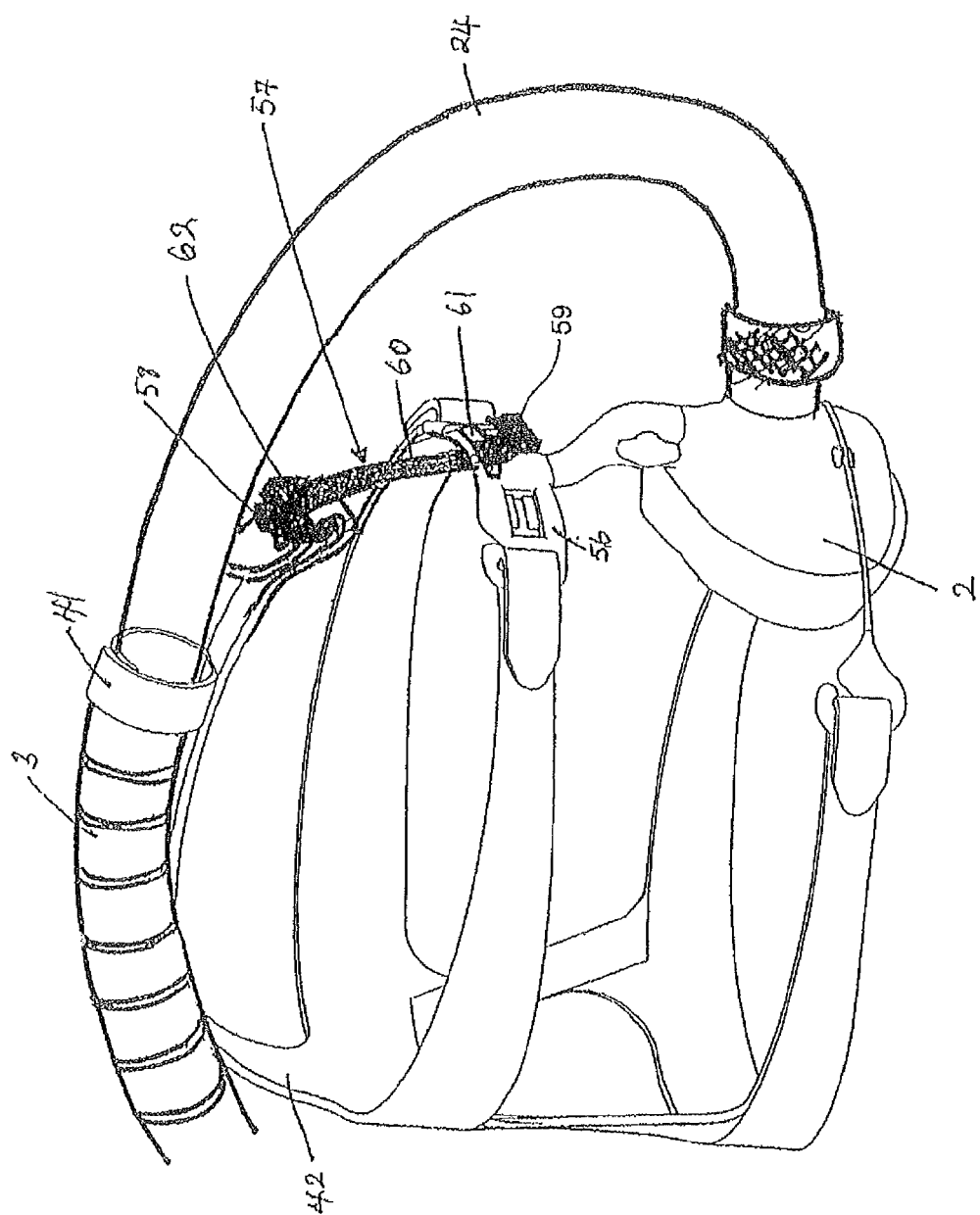
FIG. 6 is an illustration of a forth embodiment of the interface of the present invention, where a vertical glider mechanism is provided between the headgear and interface.

Another alternative embodiment is shown in FIG. 6. Here a glider mechanism is provided with the mask and headgear. The glider mechanism 57 is preferably constructed of a hard plastics material, for example, acetyl, nylon or polycarbonate or the like material, and has wide outer ends 58, 59 interconnected by a thinner central portion 60. The glider mechanism 57 may have a plurality of serrations along its length that allow it to be locked in different positions. In other forms the glider mechanism 57 may be smooth to enable it to freely move through a slot 61 provided in the forehead rest 56. The wide lower outer end 59 is permanently connected through the slot 61 in the upper portion of the forehead rest 56. A small loop 62 is permanently retained below the wide upper outer end 58 on the central portion 60 of the glider mechanism 57 for in use connection to the transverse headgear strap 42. The position of the transverse strap 42 and thus the placement of the flexible tubing 24 may be varied by raising the lower wide end 59 of the glider mechanism 57, moving it upwards such that the central portion of the glider moves through the forehead rest slot 61. When the glider mechanism 57 is lockable and when the correct adjustment has been made, the action of lowering the lower wide end 59 towards the user effectively prevents movement of the central glider portion 60 by locking the glider mechanism 57 to the slot 61 between adjacent serrations.

In yet another embodiment of the present invention as shown in FIGS. 7 and 8, the hollow body 22 of the mask 2 is connected to a single strap configured headgear 63 using a closed loop sliding strap 64. The hollow body 22 is shown having two sets of engaging clips 65, 66 which in use the closed loop sliding strap 64 snaps into place, into the both the upper 66 and lower 65 engaging clips and can only be removed by using a substantial force. This means that with any normal use the closed loop sliding strap 64 will stay retained within the engaging clips 65, 66. The closed loop sliding strap 64 is attached to the headgear by known means, one example is by a hook and loop material at the end of the strap 67, 68, but other appropriate fastening means may be used. A support strap 69, preferably made of elastic material, is preferably attached to the lower edge of the headgear 63. In other forms of the support strap 69, the strap could be made from a rigid material, such as acetyl, nylon or polycarbonate or other hard plastics materials. In use the support strap 69 attaches around the flexible tube connector 70 (for example, a connector similar to connector 44 as shown in FIG. 4) which hangs in a vertical direction below the mask inlet 23. The strap 69 in use will provide support for the connector 70 and reduce the downward drag on the mask 2 by transferring any loading on the tubing or mask to the headgear.

Alternatively, as shown in FIG. 8 the mask 2 may be connected to the different single strap configured headgear 71 using two separate sliding straps 72, 73. The upper sliding strap 72 includes a mid-section intended to reciprocate with the upper engaging clips 74, terminated at each end by full loops which attach to the upper straps 75, 76 of the headgear. The upper strap 72 is a single gliding strap. The lower sliding strap 73 is a looped sliding strap terminated at each end by single full loops which attach to the headgear lower straps 78, 79. In other forms the upper and lower straps 72, 73 may not have full loops that attach to the headgear straps but they may be a continuous strap that can pull completely through the headgear straps. The top part of the lower sliding strap 73 includes a mid-section intended to reciprocate with the engaging clips 77 and the bottom part of the lower sliding strap 73. In use the lower sliding strap 73 attaches around the flexible tube connector 80 (again, similar to that connector of FIG. 4) which hangs in a vertical direction below the inlet 23 to the mask. The bottom part of the lower sliding strap 73 in use provides support for the connector 80 and reduces the downward drag on the mask 2.

Figure 10:
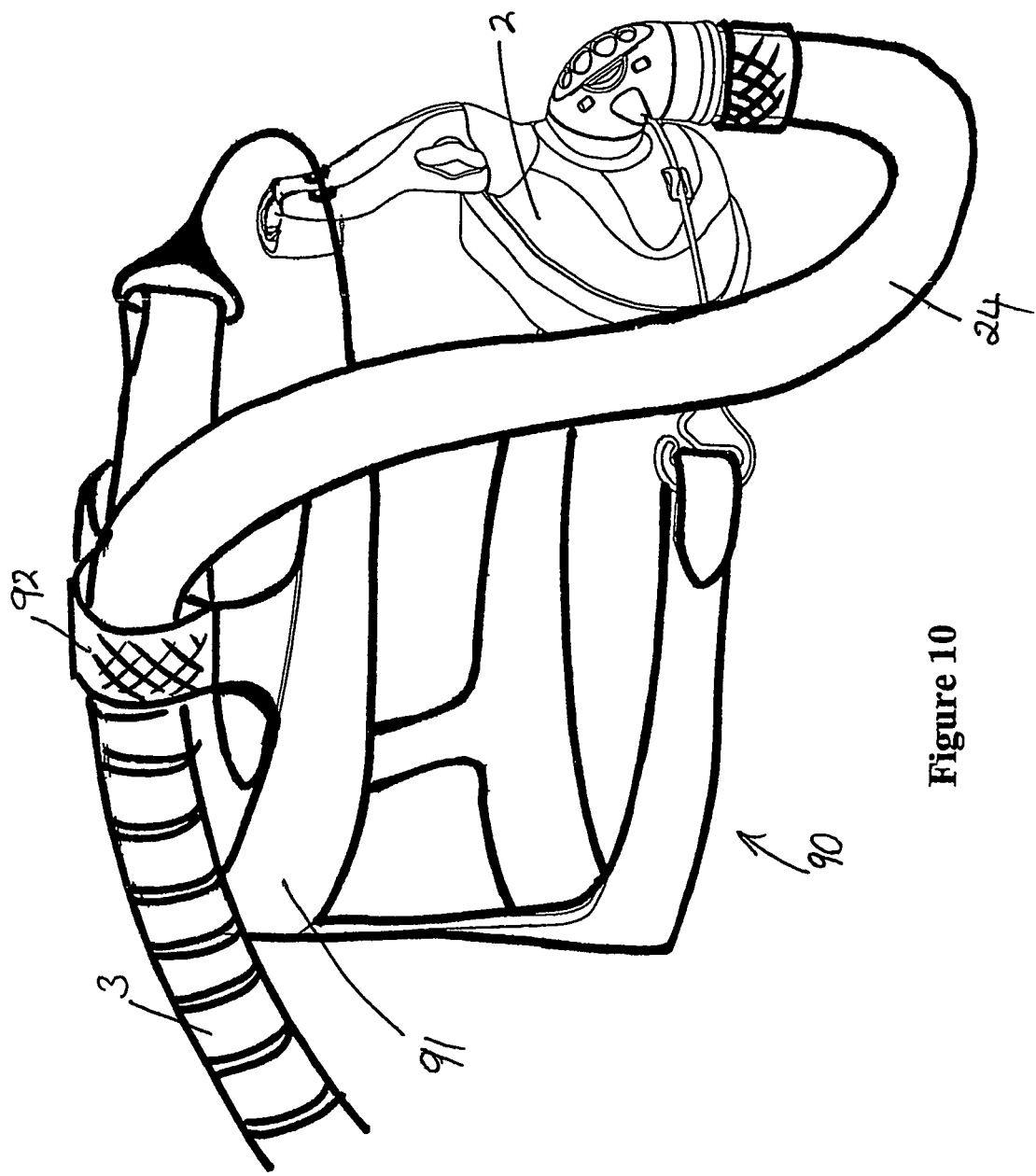
FIG. 10 is an illustration of an eighth embodiment of the interface of the present invention, where the gases conduit is threaded through a loop configuration formed on one of the headgear straps.

FIGS. 10 and 11 show further alternative forms of the interface and headgear of the present invention. FIG. 10 shows a mask 2 and headgear 90 having an upper strap 91 with a loop 92 extending from its upper edge. The loop 92 is capable of receiving the flexible tubing 24 and inspiratory conduit 3, such that the tubing or conduit can be threaded through the loop, thereby restraining the tube and/or conduit.

FIG. 11 shows a mask 2 and headgear 93 that has a similar loop to that of FIG. 10. The headgear 93 has an additional strap 95 extending between each side of the upper strap 94 of the headgear 93. Included on the additional strap 95 is a loop 96 of material (for example a loop of similar material to the headgear is sown to the strap 95) that the flexible tubing 24 and inspiratory conduit 3 are threaded through to restrain them. In FIG. 11 the flexible tubing 24 and inspiratory conduit 3 are shown disconnected, in use, the tubing and conduit would be connected after the tubing 24 is threaded through the loop 96.

Figure 12:
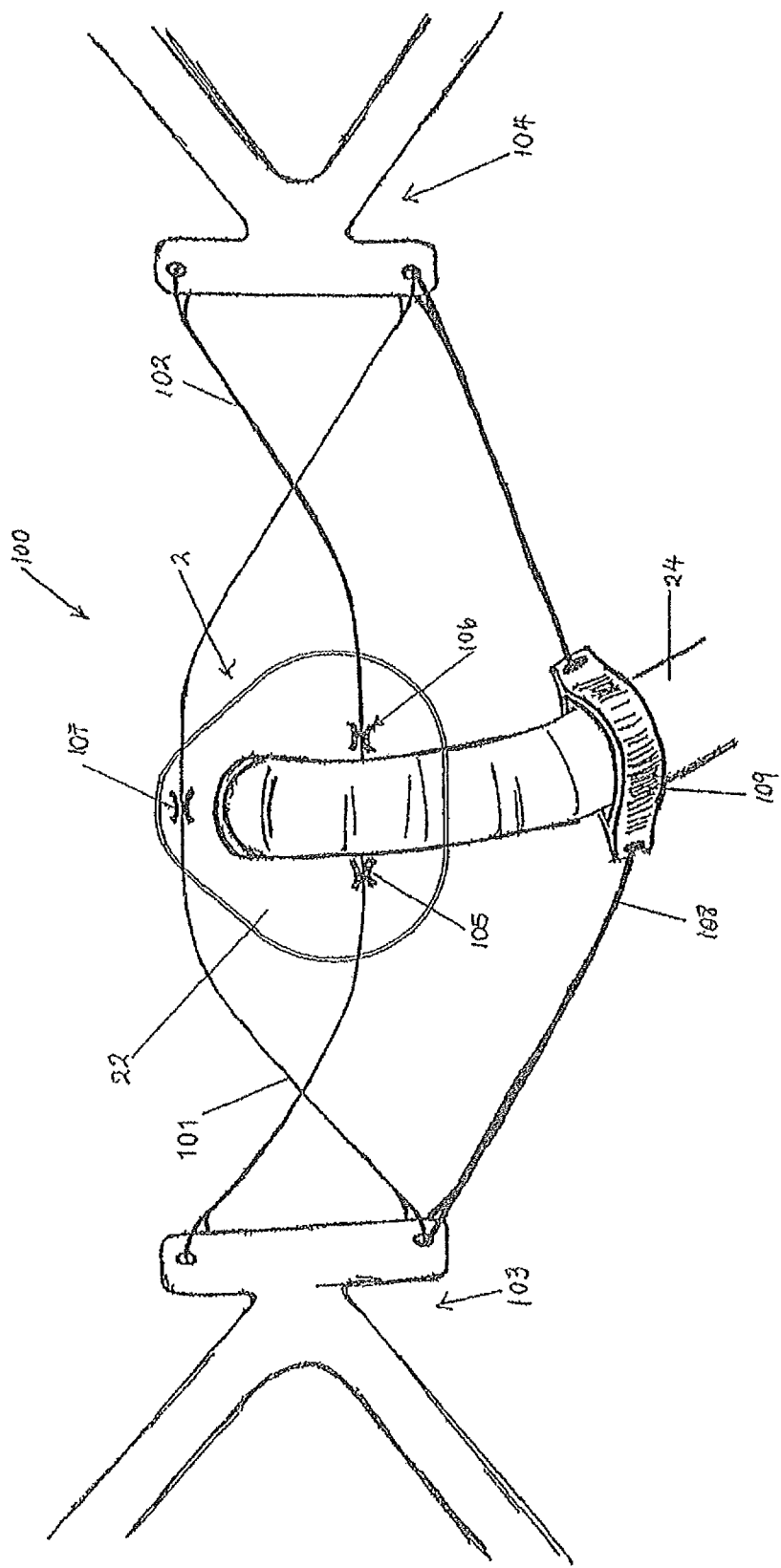
FIG. 12 is an illustration of a tenth embodiment of the interface of the present invention, where the gases conduit is restrained by a number of sliding straps.

FIG. 12 shows a tenth embodiment of the interface 100 of the present invention including headgear. The mask 2 of this embodiment is similar to that of FIGS. 7 and 8 in that it does not have an I-piece of T-piece extending upward from the mask 2. The mask 2 has a connection extending out from the mask body 22 that connects to the flexible tubing 24. The mask body 22 has on its outer surface two lower engaging clips 105, 106 and one upper engaging clip 107. The upper engaging clip 107 receives a first sliding strap 101 and the lower engaging clips 105, 106 receive a second sliding strap 102. Each of the sliding straps 101, 102 are capable of sliding horizontally over the mask body 22 when either of the headgear straps 103, 104 pull on the straps 101, 102 (in a similar manner as described with reference to the abovementioned embodiments).

The headgear straps 103, 104 also have a supporting strap 108 connected between the left side headgear strap 103 and right side headgear strap 104. The supporting strap 108 is connected midway to a connector 109 that may be slideably or permanently attached to the flexible tubing. FIG. 12 shows a slideable or moveable connector 109, but a connector similar to the flexible tube connector 70 of FIG. 7 may be provided with this embodiment.

In use, if the flexible tubing 24 is loaded, pulled or pushed the forces on the tubing 24 are transferred to the supporting strap 108, to the headgear straps 103, 104 and sliding straps 101, 102. The mask 2 is prevented from being pulled from the user's face nor the seal of the mask 2 on the user's face disrupted. In fact, in most situations when the flexible tubing 24 is loaded, pulled or pushed, the mask 2 and mask body 22 are caused by tightening of the sliding straps 101, 102 to be moved towards the user's face (that is, pulled tighter to the user's face).

In the embodiments of the mask and headgear described above the restraining of the flexible tubing 24 and inspiratory conduit 3 reduces movement of the mask 2 and breaking of the seal between the mask 2 and the user's face, when a force or load is placed on the flexible tubing 24 or inspiratory conduit 3. Further, in most cases any loading placed on the flexible tubing 24 or inspiratory conduit 3 is transferred to the sliding straps and headgear and not to the mask.

Adjustable Mask

A further embodiment of an interface and accompanying headgear of the present invention is shown in FIGS. 13 to 21. The interface 110 is shown in these figures as a nasal mask but in other forms may be a full-face mask or nasal prong type mask. The mask 110 is a hollow body 111 having a gases inlet 112 and a sealing member (or cushion) 113 which in use is configured to rest against the face of a user or patient. A conduit 114 is releaseably coupled to the gases inlet 112 of the mask 110 such that gases can be supplied to a user wearing the mask. The mask is preferably secured to the user's face by way of headgear 115 that is effectively a skull cap of the like that ensures the mask remains on the user's face in a correct position.

The conduit 114 extends upwards from the mask inlet 112 and is secured to the headgear 115 by way of support portion 116. It is preferred that the conduit 114 has a flexible (for example, corrugated) section 117 that is secured through apertures provided in either end of the support portion 116. The support portion 116 is preferably made from a flexible plastics material and is concave (or curved) in shape. The support portion 116 is a one-piece portion (although in other forms it could be a two piece portion) having a body 120 and two arms 118, 119, each with an aperture at their ends, extending out from the body 120. The upper arm 118 is narrower in width and thus is more flexible allowing to substantial movement of the conduit 114 in that region. The lower arm 119 is substantially wider in width and thickness than the upper arm 118 and is therefore more rigid, providing substantial restraint on the conduit 114 in that region.

The support portion 116 is preferably attached, by gluing, welding or other appropriate fastening means, substantially at the body 120 region to the headgear 115 (more particularly, to the forward substantially rigid part 135 of the headgear 115). In other forms the support portion may be integrally moulded with the headgear or could be connected to the headgear at any other appropriate or feasible location.

The flexible conduit section 117 and curved support portion 116 effectively decouple movement of the conduit 114 from the mask 110. Furthermore, the support portion 116 lifts the conduit 114 off the user's head reducing annoyance and increasing comfort to the user. Therefore, the support portion and conduit extending over the head reduce movements in the mask as the patient moves in bed and the seal between the mask 110 and the user is maintained.

Figure 22:
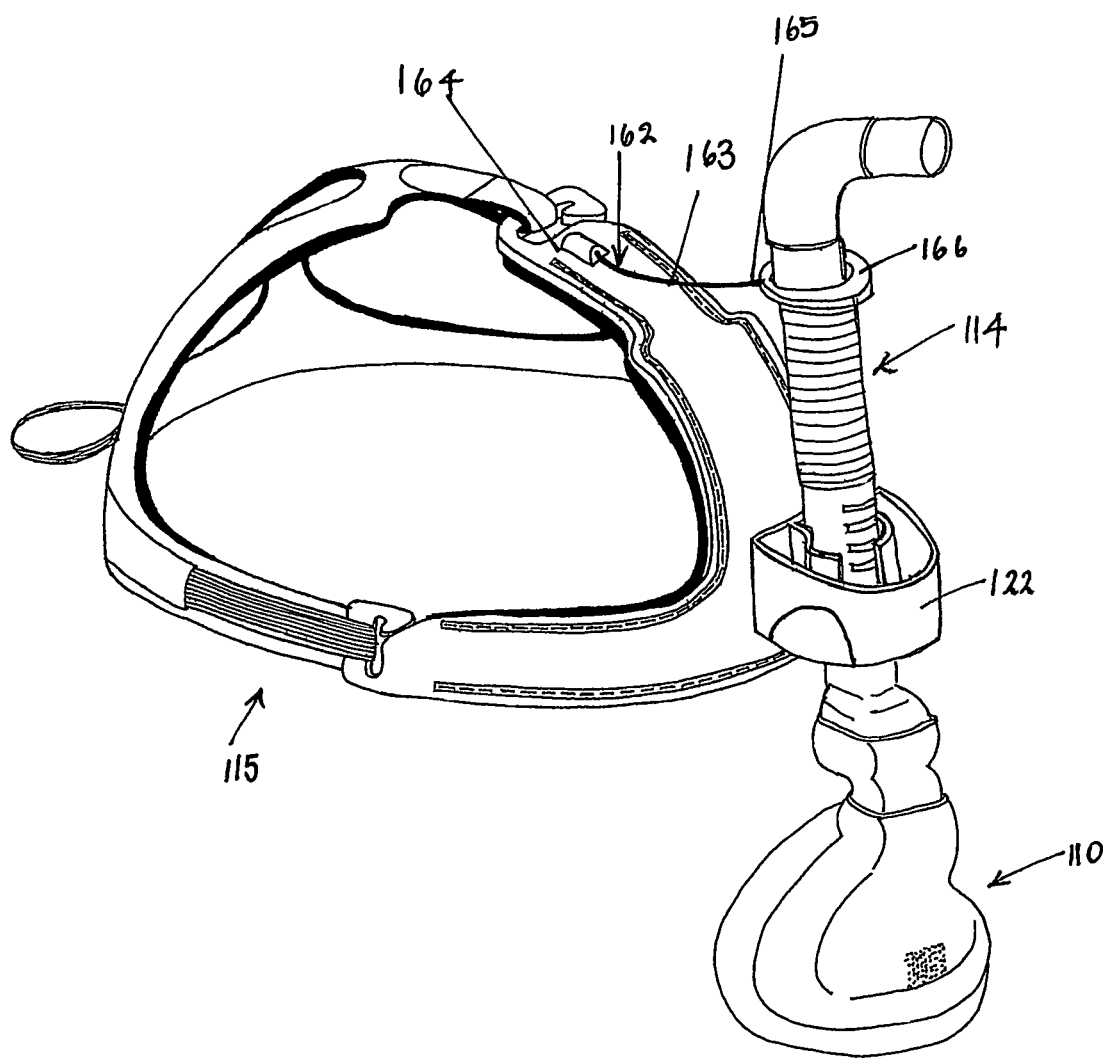
FIG. 22 is a further embodiment of an interface and headgear of the present invention showing an alternative embodiment of a support portion that supports an inlet conduit to the interface.
Figure 23:
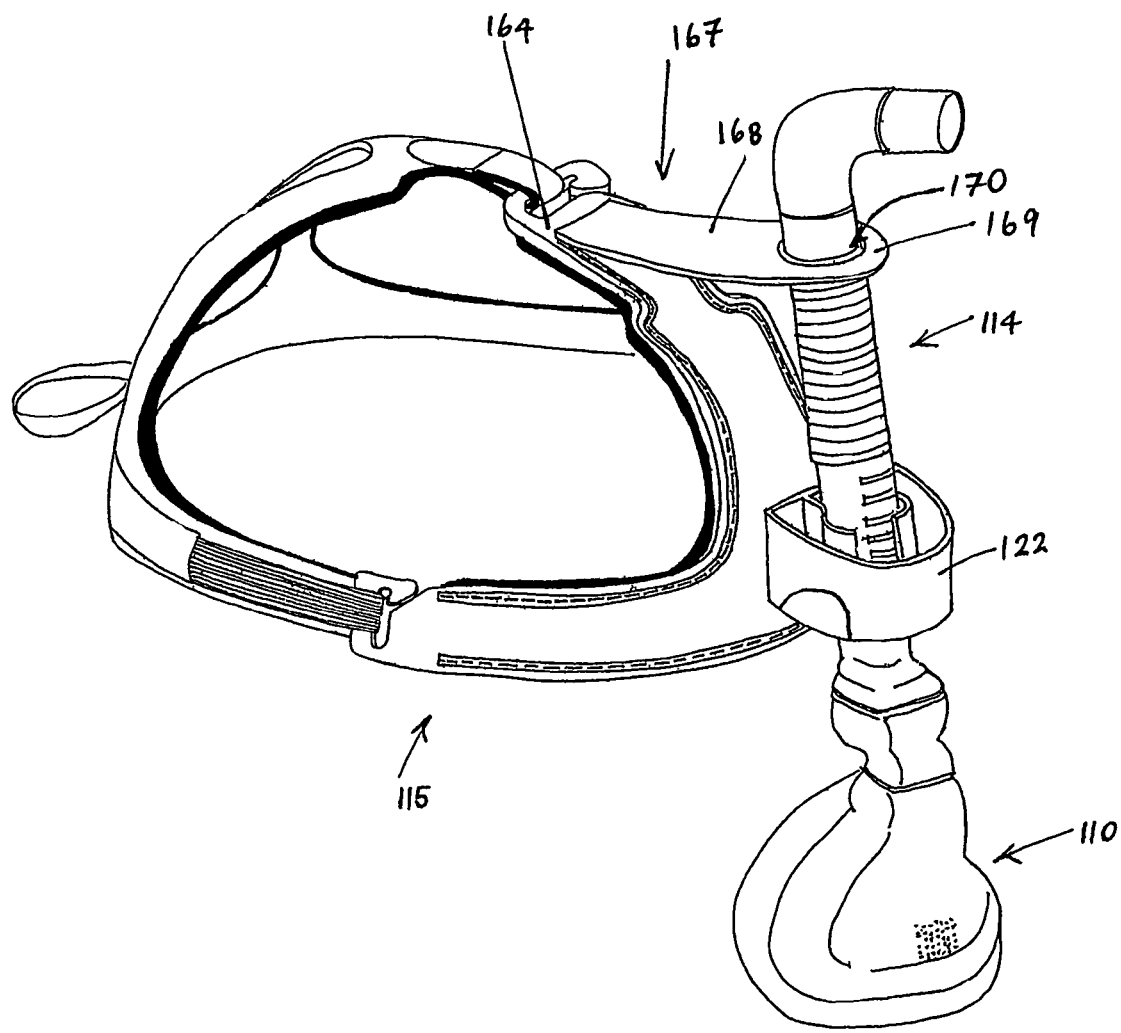
FIG. 23 is yet a further embodiment of a support portion for the inlet conduit.

Alternative embodiments of the support portion described above are shown in FIGS. 22 and 23. In FIG. 22, the support portion 162 is a flexible link 163, such as a wire, line, lead or cable, attached to the transverse headgear strap 164 by way of moulding, gluing, welding or the like. At the distal end 165 of the link 163 is a loop 166 which the conduit 114 is secured through. The loop 166 is preferably made from a plastics material but may be made from other appropriate materials, such as rubber, silicone or various metals. In FIG. 23 the support portion 167 is an elongated flange 168 extending out from the transverse headgear strap 164. At the flanges distal end 169 there is an aperture 170 that receives the conduit 114. The flange 168 is preferably made from a flexible plastics material, but may be made of other appropriate material, such as metal or the like.

In both of these embodiments the support portions 162, 167 support and decouple the conduit 114 from the mask 110.

In the embodiment described above of the present invention the mask 110 is adjustable on a user's face in more than one direction. Firstly, referring to FIGS. 13, 20 and 21 the vertical position of the mask 110 can be adjusted, such that the distance between the headgear 115 and the mask 110 may be increased or decreased to enable custom fitting to a user. Extending from the mask gases inlet 112 is a cylindrical inlet conduit 121 that attaches (in a fixed or releasable manner) to the inspiratory conduit 114. The inlet conduit 121 is substantially restrained against the forward rigid part 135 of the headgear 115 by a housing 122. The inlet conduit 121 extends through the housing 122 and is capable of sliding through the housing 122. The housing 122 is a substantially cylindrical extension extending from the headgear 115 that has been glued, welded or similarly fastened to, or integrally moulded with the forward substantially rigid part 135 of the headgear 115. The inlet conduit 121 has a series of detents 123 formed along its length that interact with an inner protrusion extending from the inside of the housing 122. To disengage the protrusion from any one of the detents 123 the housing 122 may be squeezed at its sides, in regions 124 and 125, thereby deforming the housing 122 and causing the protrusion to move out of the detent it was fitted in. To adjust the height of the mask 110 a user or caregiver may simply place an upward or downward pressure on the mask 110 and simultaneously squeeze the sides of the housing 122. The inlet conduit 121 may then be slid up or down within the housing 122 until an appropriate position is found, then the sides of the housing 122 are released, causing the protrusion to enter an appropriate detent. The inlet conduit 121 is thus effectively locked in that position by the protrusion and detent interaction.

In other embodiments of the mask and headgear the height adjustment mechanism may be a threaded adjustment between a housing similar to that described above and a threaded inlet conduit, a frictional sliding mechanism between a housing and the inlet conduit or a teethed sliding mechanism between the housing and inlet conduit.

Figure 21:
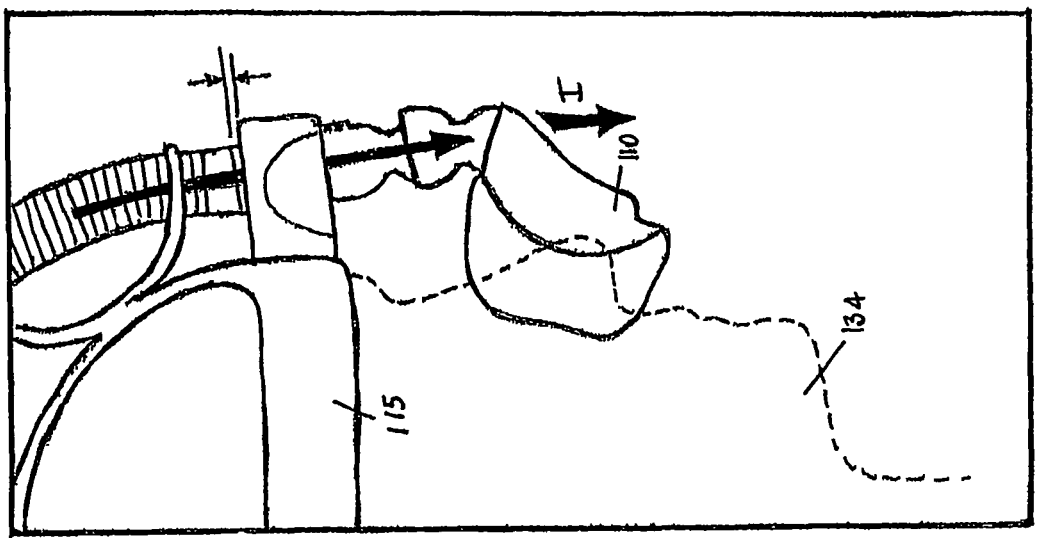
FIG. 21 is a further illustration of the interface in a different position after adjustment of its height in relation to the headgear.
Figure 20:
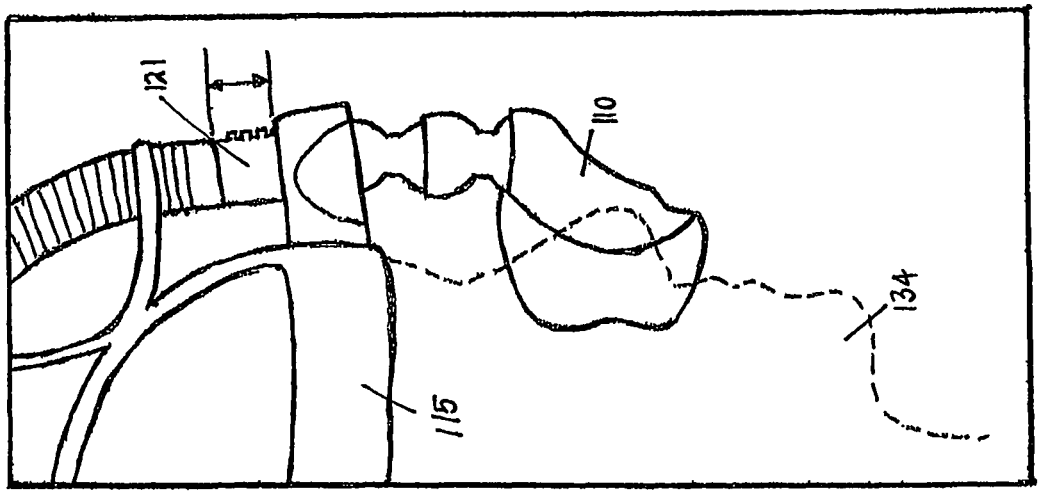
FIG. 20 is an illustration of the interface of FIG. 13 in use particularly showing the housing and the conduit that allows for adjustment the height of the interface in relation to the headgear.

FIGS. 20 and 21 show the mask 110 on a user 134 where the mask 110 has been moved downwards in the direction of arrow I by the sliding of the inlet conduit 121 within the housing 122.

Figure 14:
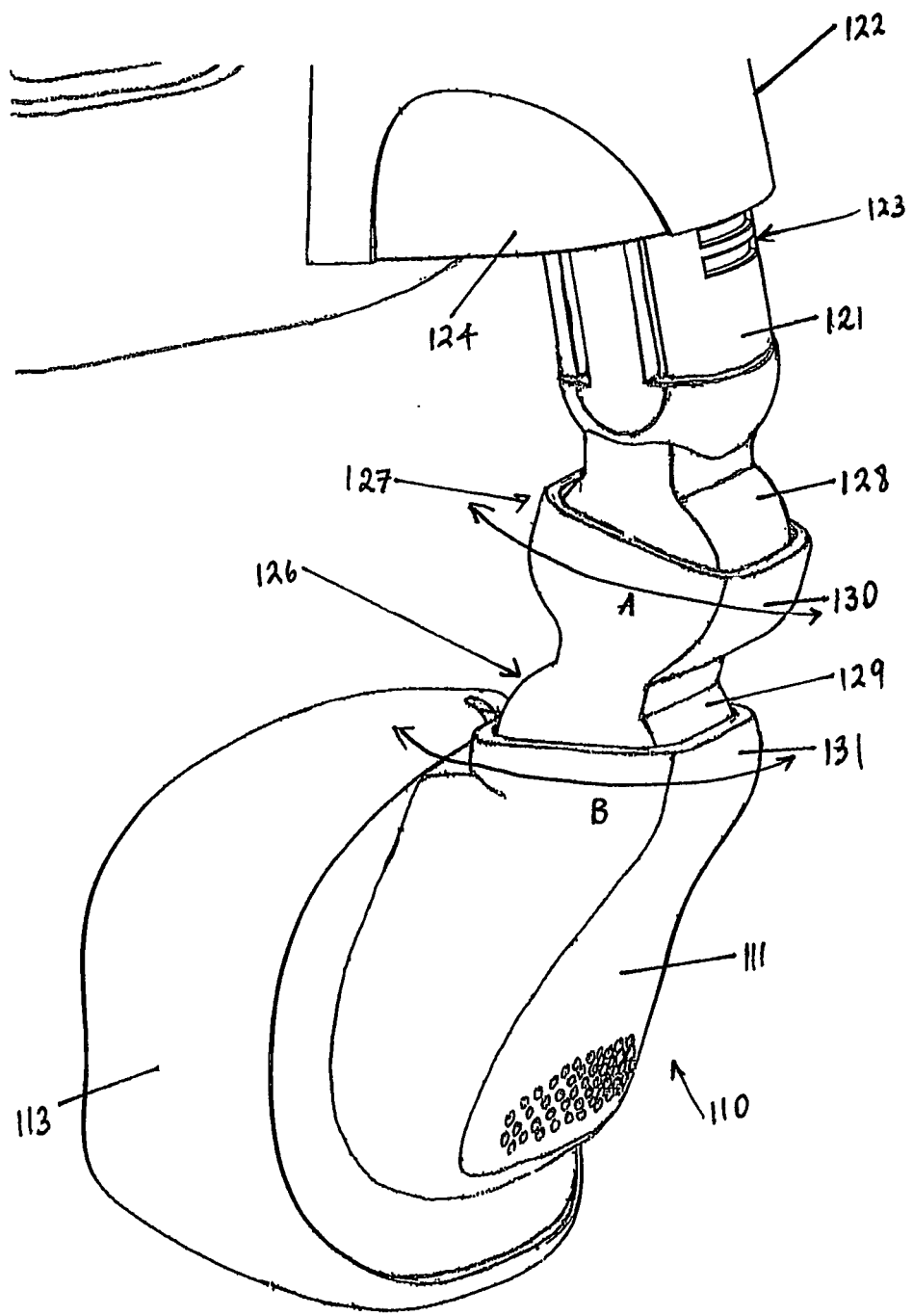
FIG. 14 is a close-up view of the interface of FIG. 13, showing an interface angle adjustment mechanism.

The angle of the mask 110 on the user's face may also be adjusted by the use of at least one ball and socket joint. In FIG. 14, two joints 126, 127 are shown, it is preferred that the mask 110 is provided with at least one joint, but any number of joints may be used. The joints 126, 127 are formed in a hard plastics material such as polycarbonate, acetyl or polyurethane and are each made up of a ball part 128, 129 and socket part 130, 131. Each of the ball parts 128, 129 fit within the respective socket part 130, 131, yet the ball parts 128, 129 are able to swivel within the socket parts 130, 131. In the preferred form of the mask and headgear of the present invention the ball and socket joints 126, 127 have a rectangular profile, such that only movement in one axis (per joint) is allowed. For example, the first joint 127 is capable of moving the mask 110 and thus the second joint 128 in the direction of arrow A. The second joint 126 is capable of moving the mask 110 in the direction of arrow B.

Figure 19:
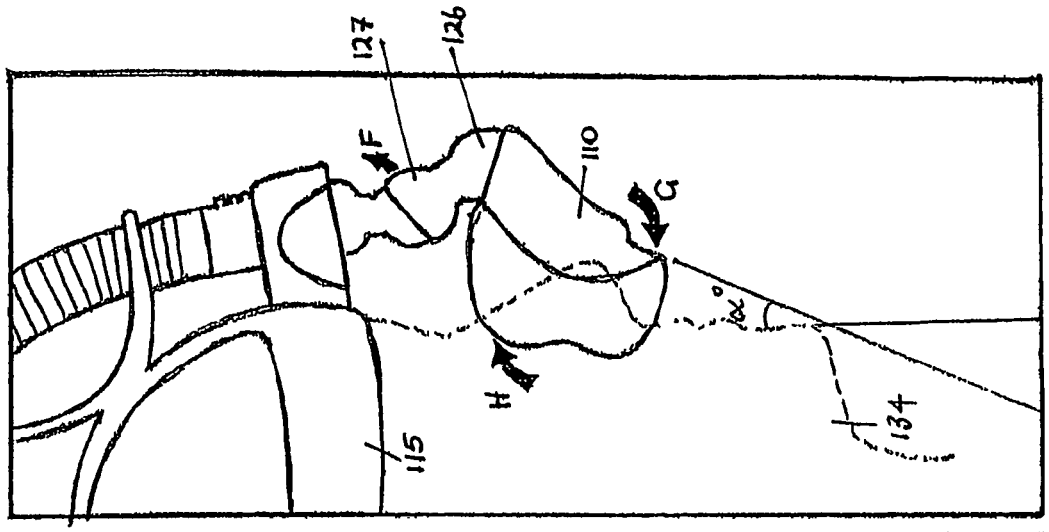
FIG. 19 is yet a further illustration of the interface of FIG. 13 in use after the interface has been further adjusted using the jointed mechanism.
Figure 18:
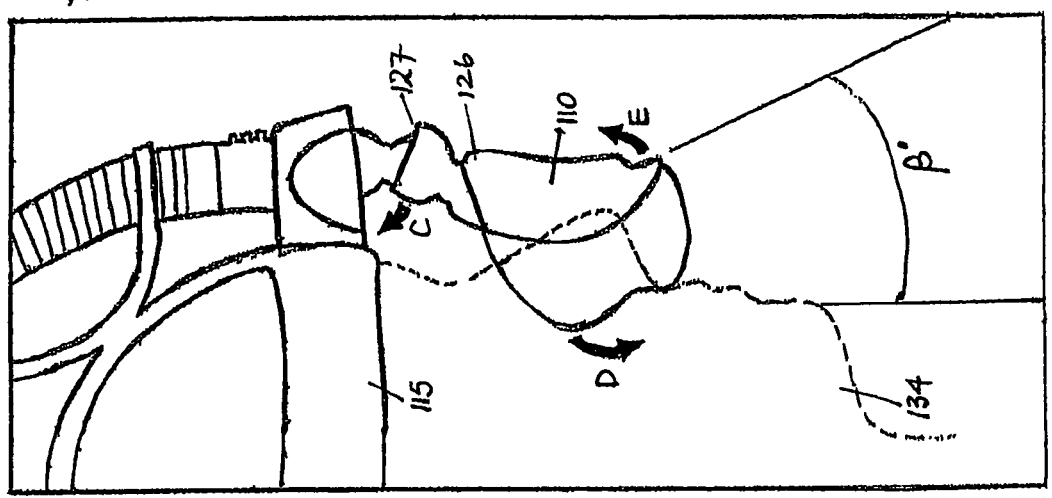
FIG. 18 is a further illustration of the interface of FIG. 13 in use after the interface has been adjusted using the jointed mechanism, to better fit the user.
Figure 17:
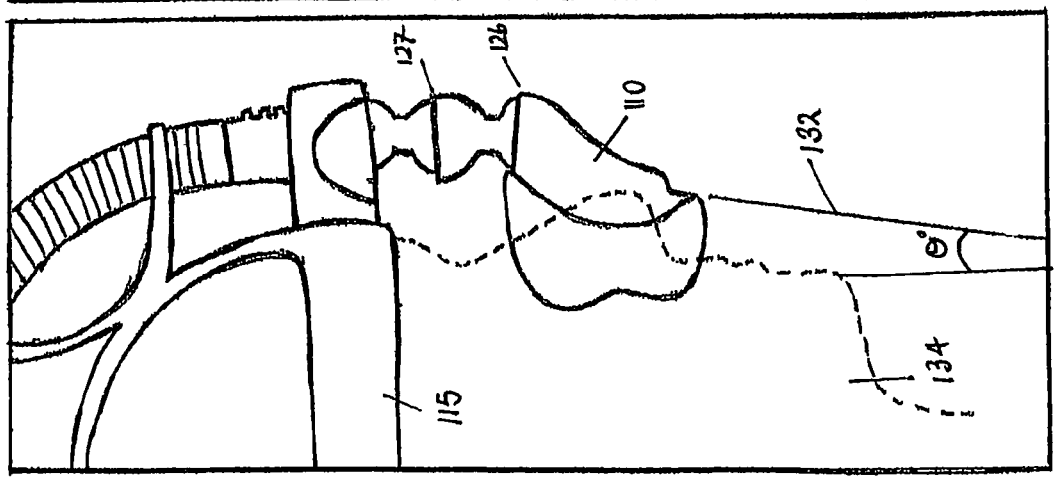
FIG. 17 is an illustration of the interface of FIG. 13 in use.

FIGS. 17, 18 and 19 show the movement of the mask 110 in relation to a user 134. In FIG. 17 shows an axis 132 through the mask 110 is shown to be at an angle θ to a straight line 133 drawn extending from the chin of the user 134. In FIG. 18 the mask 110 has been altered to sit differently on the user 134. Firstly the first joint 127 has been swiveled back in the direction of arrow C and the second joint 126 swiveled forward, such that the mask 110 moves down and out in the directions of arrows D and E respectively. Therefore, the angle between the line 133 and 132 has changed to angle β which is larger than angle θ. In FIG. 19 the mask 110 has been altered to sit yet different again on the user's face 134. The first joint 126 has been swiveled forward in the direction of arrow F and the second joint 126 swiveled back towards the user's face, such that the mask 110 moves back and upwards in the directions of arrows G and H respectively. The angle α between the line 133 and 132 is now a negative angle compared to that in FIGS. 17 and 18.

The position of the mask 110 may be adjusted on a user in the manner described above so as to achieve a more comfortable fit for the user or to ensure a proper seal of the mask 110 on the user's face.

In the preferred form of the mask and headgear of the present invention the joints 127, 128 when swivelling are a tight fit such that a interference friction between the ball and socket occurs and this holds the mask 110 in the position placed in after adjustment of the joints. In other forms, the joints may have locking mechanisms such as a lip and protrusion or teeth locking mechanisms.

Figure 24:
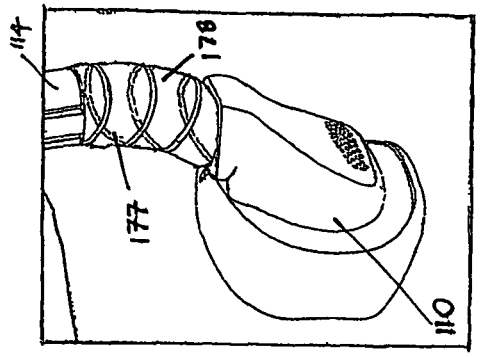
FIG. 24 is further embodiment of an interface angle adjustment mechanism, particularly a section of flexible tube with a malleable band.
Figure 25:
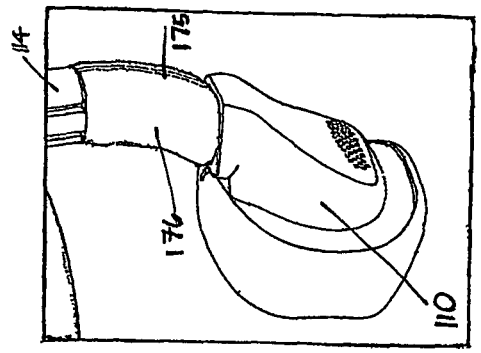
FIG. 25 is yet a further embodiment of an interface angle adjustment mechanism, where the malleable band sits over the section of flexible tube.
Figure 26:
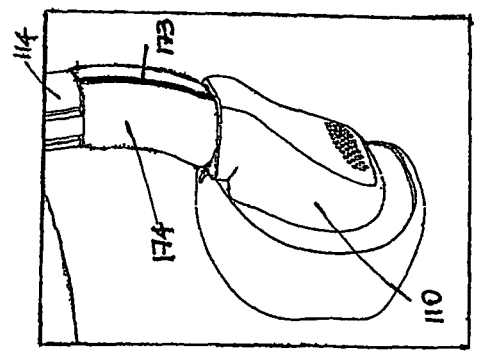
FIG. 26 is yet a further embodiment of an interface angle adjustment mechanism, where the malleable band is moulded within the section of flexible tube.
Figure 27:
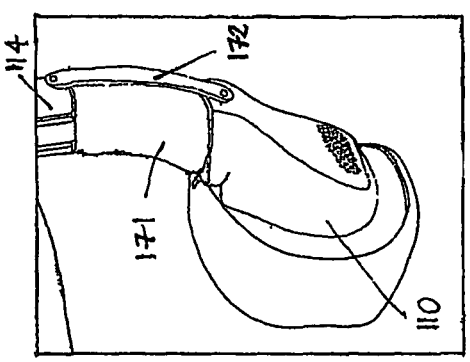
FIG. 27 is yet a further embodiment of an interface angle adjustment mechanism, where a spiral wire is moulded into or resides within the section of flexible tube.
Figure 30:
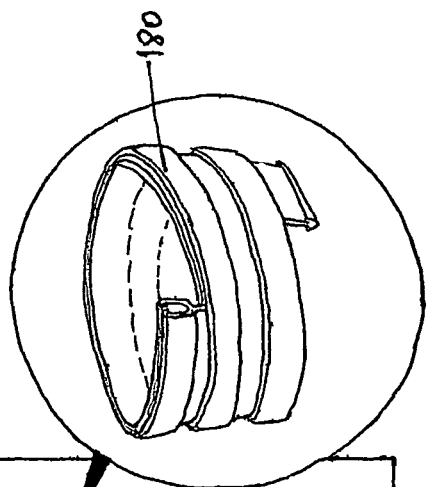
FIG. 30 is a close-up view of a portion of the extendable spiral tube of FIG. 29.
Figure 29:
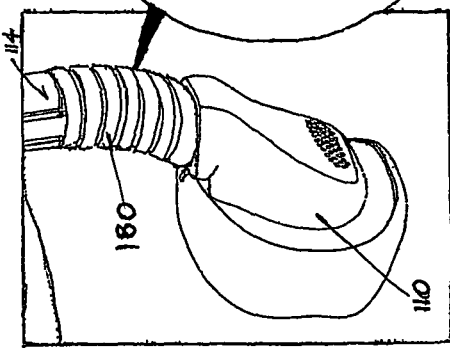
FIG. 29 is still a further embodiment of an interface angle adjustment mechanism, where a section of extendable spiral tube is provided.
Figure 28:
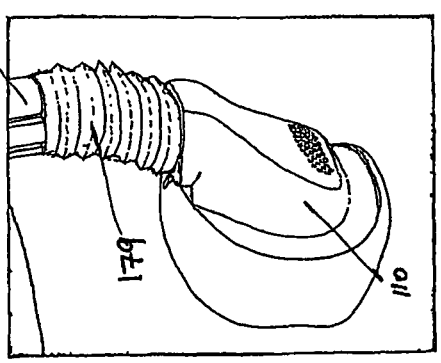
FIG. 28 is yet a further embodiment of an interface angle adjustment mechanism, where a section of concertina or extendable tube is provided.

Other embodiments to the ball and socket jointed adjustment are shown in FIGS. 24 to 30. FIG. 24 shows an embodiment where the mask angle adjustment mechanism is a section of flexible (for example, silicone, rubber or similar material) tubing 171 connected between the mask 110 and conduit 114. The section of tubing 171 is reinforced by a malleable band or bridge 172 pinned across the section of tubing 171. Preferably the malleable band is made from a malleable metal. To adjust the mask 110 the flexible tubing 171 and band 172 can be bent to an appropriate position and the band 172 would hold the position the mask was placed in. FIGS. 25, 26 and 27 show similar embodiments that would work in the same manner as the embodiment of FIG. 24. In FIG. 25 a malleable band 173, such as a wire or metal band, may extend along the outside of the flexible tube 174, or in FIG. 26 the malleable band 175 may be moulded within the flexible tube 176. In FIG. 27 a spiral wire 177 may be moulded within a flexible tube 178 or merely reside within the flexible tube. FIG. 28 shows a concertina or extendable tube 179 that would act as the mask angle adjustment mechanism. A user could adjust this tube 179 to move the mask into an appropriate position. Here, the tube 179 would have to be made from a substantially rigid material that retained the shape it was moved into. In FIGS. 29 and 30 the mask angle adjustment mechanism is a section of extendable spiral tube 180. This tube 180 is preferably extruded and must be of a substantially rigid material such that it retains its shape when moved.

Figure 13:
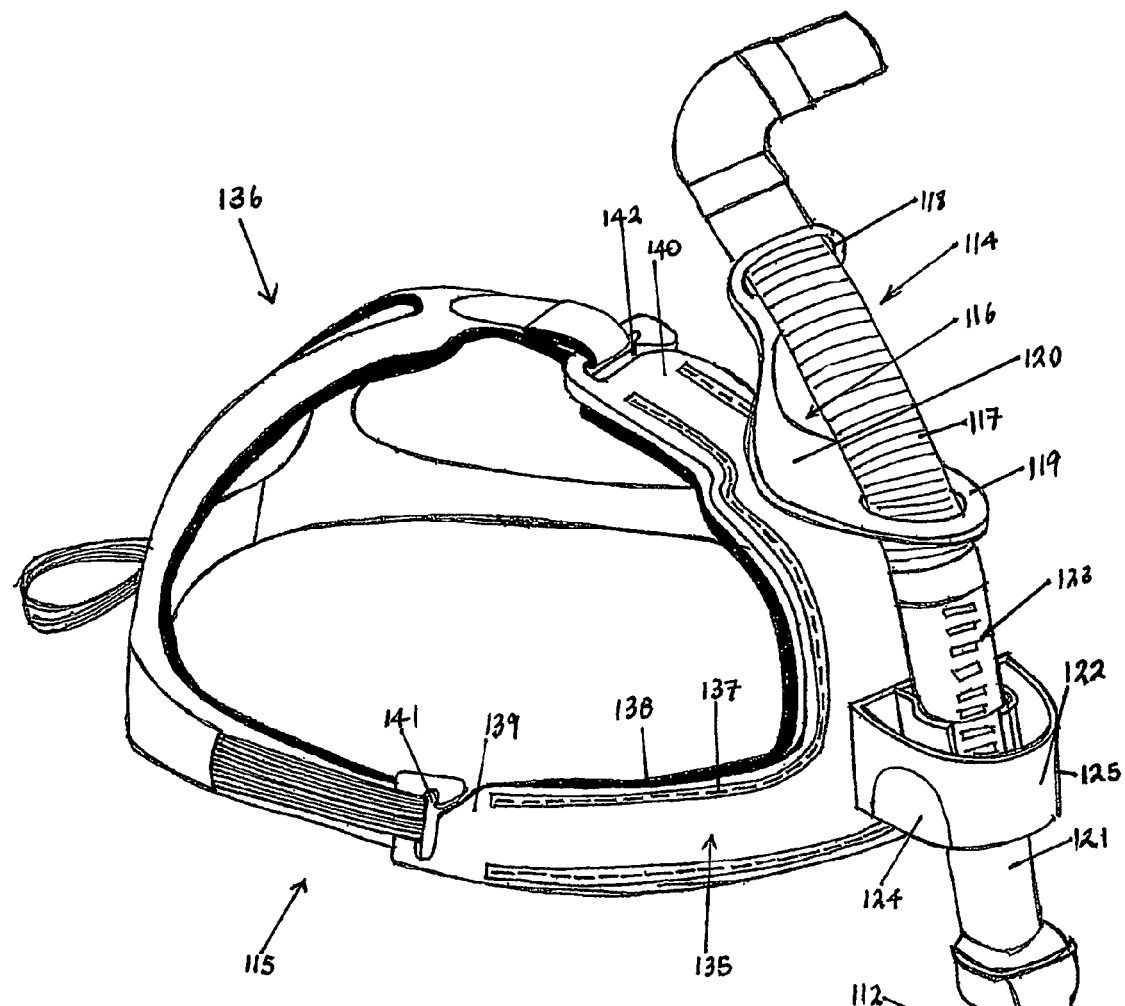
FIG. 13 is an illustration of an eleventh embodiment of the interface and headgear of the present invention, where the gases conduit is restrained by a housing which the conduit may be moved through in order to adjust the height of the interface.

The headgear of the present invention will now be described with reference to FIGS. 13 and 15. As discussed above the headgear 115 is of a partial skull cap type and is comprised of a forward substantially rigid part 135 and backward soft part 136. The forward substantially rigid part ("forward part") 135 is preferably an inverted T-shape. The forward part 135 comprises a substantially rigid layer 137 that has been moulded from a flexible polymer (such as polyurethane, polyester blend, rubber or copolyester elastomers) and a padding layer 138. Here when reference is made to substantially rigid this means that this part of the headgear is more rigid compared to the other parts of the headgear, it must be appreciated that the forward part 135 can be flexed. The padding layer 138 is preferably made from a soft fabric, such as laminated polyurethane foam, lycra, loop or polyurethane foam, silicone plastic, thermoplastic rubber, polyester, or Spandex™. Preferably the padding layer is made from a breathable fabric, such as Breathoprene™. The padding layer 138 is preferably stitched to the rigid layer 137, but in other forms a padded sleeve may be provided which can be removed from the rigid layer and washed. In yet other forms the padded layer may be attached by buttons, hook and loop fastener or domes to the rigid layer.

The forward part 135 is attached to the backward soft part ("soft part") 136 by appropriate attachment means. As shown in FIG. 13 the ends 139, 140 (of which only 2 of a possible 3 ends are shown) are formed with a partial loop or hook 141, 142, that part of the soft part 136 of the headgear can be looped over. In other forms other attachment means may be provided, such as hook and loop fastener, button and dome configurations.

In yet other embodiments of the present invention the headgear may be made up of a one piece skull cap, where a forward substantially rigid part is attached to the skull cap.

Figure 15:
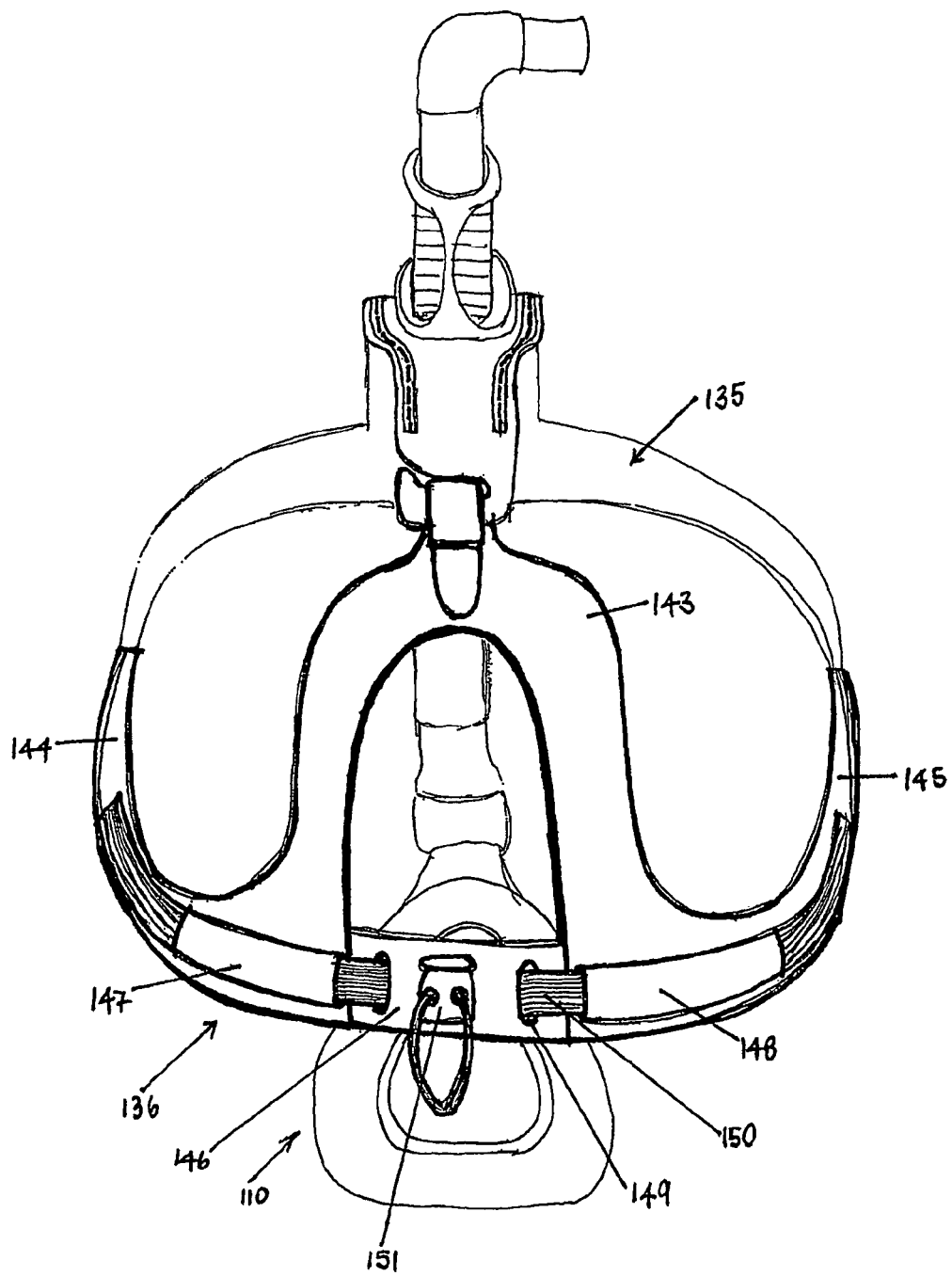
FIG. 15 is a rear view of the headgear of the interface and headgear of FIG. 13.

Referring now to FIG. 15, the backward soft part 136 will now be described in more detail. The soft part 136 comprises an inverted U section 143 that has arms 144, 145 extending sideways from the U. The arms 144, 145 are bridged by an additional stretchable section 146. The U section 143 and arms 144, 145 are made from a stretch material, such as, elastic, silicone rubber, laminated material, low density polyurethane foam, lycra laminate, polyester, nylon, Spandex™, lycra or Breathoprene™. The stretchable section 146 is made from a similar material that is capable of stretching more than the breathable material making up the U section 143 and arms 144, 145. Both of these sections are preferably made from a breathable stretch material, such as, Breathoprene™. The stretchable section 146 and arms are formed with sleeves 147, 148, 149 capable of receiving and having a length of elastic 150 threaded through them. The elastic 150 is preferably attached to the hooks 141, 142 of the forward part 135 and loops through a toggle 151 positioned at the stretchable section 146 at the back of the headgear 115. In use, a user may tighten the headgear 115 by pulling the loop of elastic 150 through the toggle causing the soft part 136 of the headgear to be tightened in relation to the forward part 135 of the headgear.

Figure 16:
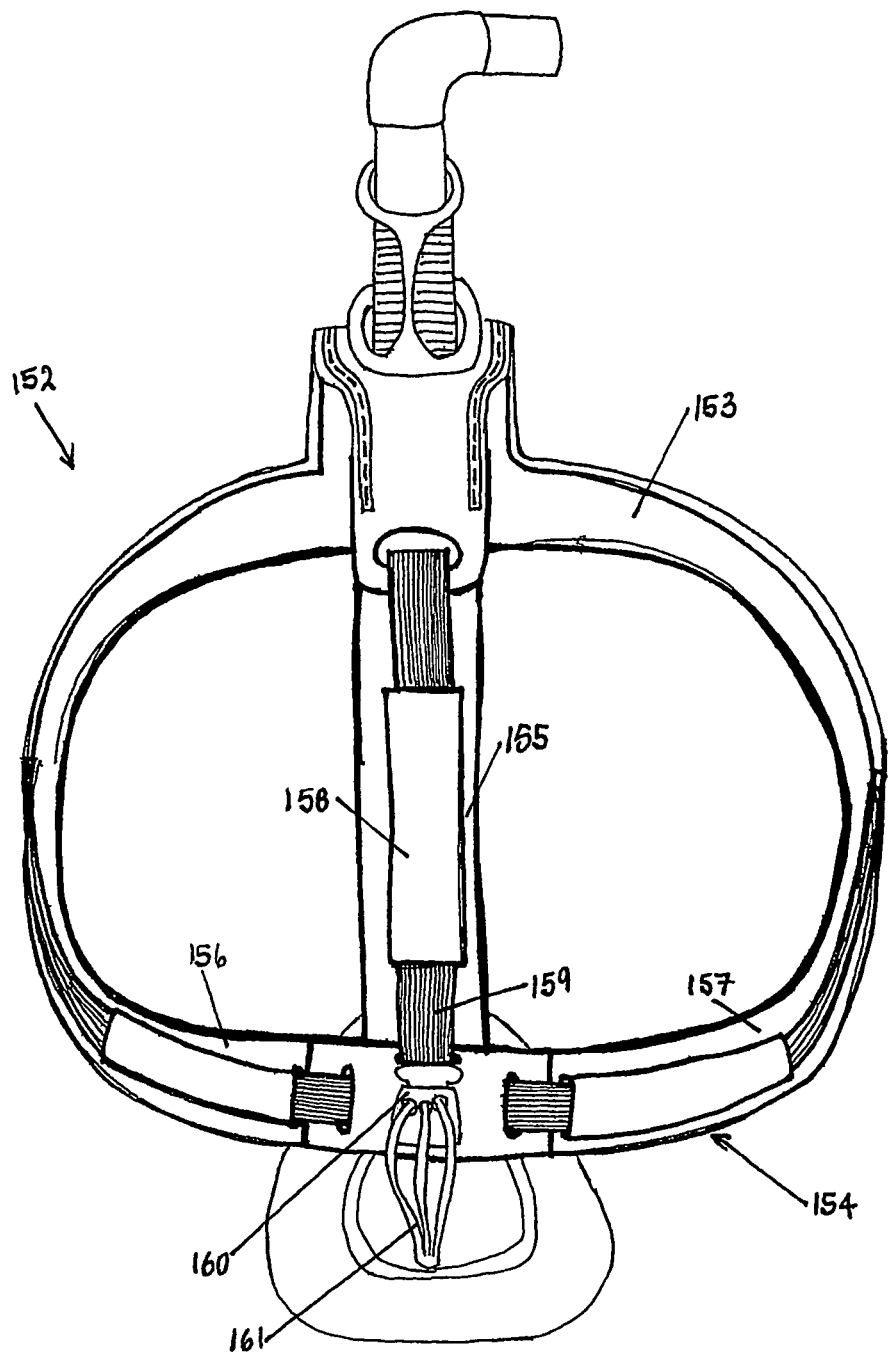
FIG. 16 is an alternative embodiment of the headgear of FIG. 13.

In other forms of the present invention the headgear may be in the form as shown in FIG. 16. In this form the headgear 152 comprises a forward part 153 and backward soft part 154 similar to that described above but the backward soft part 154 has a different form. Instead of being U shaped the soft part 154 is an inverted T shape, having a centre arm 155 and two side arms 156, 157. The side arms 156, 157 can be tightened in relation to the forward part 153 as described above, but additionally the centre arm 155 may also have a sleeve to receive an additional length of elastic 159 in order to tighten this arm in relation to the forward part 153. The length of elastic 159 would extend into the toggle 160 and be tightened at the same time as the side elastic lengths when the user pulled the loop of elastic 161 through the toggle 160.

One of the major advantages of the mask and headgear of the present invention is that all the adjustments of the mask or headgear described above can be made by the user when the headgear and mask is in use on the user's head and face. Therefore, this greatly improves the ease of use of the mask and headgear and allows for easy and correct adjustment of the mask and headgear, providing added comfort to the user.

We claim:

1. A device for delivering a supply of gases to a user comprising:

an interface including a hollow body and at least one engaging clip, a gases inlet in said hollow body, and a sealing member configured to in use rest against the face of a user, the interface adapted in use to supply gases to said user, a headgear adapted to be positioned around the head of said user, said headgear including a projecting section;

an interface strap configured to connect the projecting section to the interface, wherein the interface strap is configured to reciprocate relative to the at least one engaging clip and is capable of sliding relative to the interface;

a conduit supplying said gases to said interface, said conduit attached to said gases inlet and a non-adjustable support strap attached to said projecting section, said support strap forming a loop to connect to and support said conduit, said support strap connecting to said conduit below the gases inlet as said conduit hangs vertically below said gases inlet, said support strap supporting said conduit such that said conduit hangs away from said headgear and interface and such that at least a portion of a downward load applied to said conduit transfers through said support strap, said projecting section, and said interface strap to apply a force to said interface to draw at least a portion of the interface toward the user headgear;

wherein the interface strap and the support strap are a single strap.

2. A device according to claim 1 wherein said headgear is comprised of a forward substantially rigid part and a backward soft part.

3. A device according to claim 2 wherein said forward substantially rigid part includes a substantially rigid layer and a padding layer, said padding layer is removable from said rigid layer.

4. A device according to claim 2 wherein said backward soft part is formed of a stretchable, breathable material.

5. A device according to claim 1 wherein said headgear includes tightening means that allows the adjustment of a backward soft part, said tightening means is a length of elastic attached to a forward substantially rigid part but extending over said backward soft part and a toggle which said length of elastic is capable in use of being pulled through to tighten said backward soft part in relation to said forward substantially rigid part.

6. A device as claimed in claim 1 wherein said support strap is a sling connecting to the projecting section and said conduit.

7. A device as claimed in claim 1 wherein said support strap is a sliding strap that connects to the projecting section and said conduit, allowing a sliding connection between said headgear and said conduit, said sliding connection reducing drag and other forces on said mask or headgear due to said conduit moving.

8. A device as claimed in claim 1 wherein there is a sliding connection between said headgear and said interface when said interface is engaged with said user.

9. A device as claimed in claim 1 wherein a first end of said support strap connects to one side of said headgear, a second end of said support strap connecting to said opposite side of said headgear at said first end of said support strap, said strap extending below said gases inlet, said strap arranged to form a loop and connect to said conduit below said gases inlet.

10. A device as claimed in claim 1 wherein said headgear is connected to said interface by two interface straps, said interface straps preventing said interface from being pulled from a said user's face and preventing the sealing member from being dislodged.

11. A device as claimed in claim 1 wherein said conduit includes a flexible tube connector, said support strap is connected to said flexible tube connector to support said conduit.

12. A device as claimed in claim 1 wherein said support strap connects to said conduit below a location where said support strap connects to said projecting section.

13. A device as claimed in claim 12 wherein said support strap connects to said conduit below said headgear.

14. A device as claimed in claim 1 wherein said support strap attaches to a lower edge of the projecting section.

15. A device as claimed in claim 1 wherein said headgear is adapted to be positioned around only the back of the head of said user.

* * * * *